(12) United States Patent
Broekaert et al.

(10) Patent No.: US 6,521,590 B1
(45) Date of Patent: *Feb. 18, 2003

(54) BIOCIDAL PROTEINS

(75) Inventors: Willem Frans Broekaert, Dilbeek (BE); Bruno Philippe Angelo Cammue, Alsemberg (BE); Rupert William Osborn, Twickenham (GB); Sarah Bronwen Rees, Forest Park (GB); Jozef Vanderleyden, Heverlee (BE)

(73) Assignee: Zeneca, Ltd., Bracknell (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/298,574

(22) Filed: Apr. 29, 1999

Related U.S. Application Data

(63) Continuation of application No. 08/777,113, filed on Dec. 30, 1996, now Pat. No. 5,986,176, which is a division of application No. 08/451,566, filed on May 26, 1995, now Pat. No. 5,691,199, which is a division of application No. 08/149,839, filed on Nov. 10, 1993, now Pat. No. 5,514,779, which is a continuation-in-part of application No. 08/002,842, filed on Jan. 14, 1993, now abandoned, which is a continuation-in-part of application No. PCT/GB92/00999, filed on Jun. 3, 1992.

(30) Foreign Application Priority Data

| Jun. 7, 1991 | (GB) | 9112300 |
| Jun. 7, 1991 | (GB) | 9112300 |
| Nov. 12, 1992 | (GB) | 9223708 |
| Nov. 12, 1992 | (GB) | 9223708 |
| Feb. 23, 1993 | (GB) | 9303564 |
| Feb. 23, 1993 | (GB) | 9303564 |

(51) Int. Cl.[7] .................. A61K 38/08; A61K 38/10; A61K 38/16; C07K 4/00; C07K 14/00
(52) U.S. Cl. ............ 514/2; 530/300; 530/350; 530/328; 514/2; 514/16
(58) Field of Search ................. 530/300, 350; 514/2, 16

(56) References Cited

U.S. PATENT DOCUMENTS

| 4,617,149 A | 10/1986 | DiMarchi et al. |
| 4,940,840 A | 7/1990 | Suslow et al. |
| 5,187,262 A | 2/1993 | Raikhel et al. |
| 5,194,596 A | * 3/1993 | Tischer et al. |
| 5,350,836 A | * 9/1994 | Kopchick et al. |
| 5,399,668 A | 3/1995 | Raikhel et al. |
| 5,482,928 A | 1/1996 | DeBolle et al. |
| 5,514,779 A | 5/1996 | Broekaert et al. |
| 5,538,525 A | 7/1996 | Broekaert et al. |
| 5,597,801 A | 1/1997 | Broekaert et al. |

OTHER PUBLICATIONS

Benjamin et al., 1998, Development 125:1591–1598.*
Vukicevic et al., 1996, PNAS USA 93:9021–9026.*
Massague, 1987, Cell 49:437–438.*
Pilbeam et al., 1993, Bone 14:717–720.*
Bowie et al., Science 247:1306–1310, 1990.*
Shinshi et al, 1990, Plant Mol. Biol. 14, 357:368.
Boller et al., 1983, Planta 157:22–31.
Watson et al., 1987, Molecular Biology of the Gene, 4th ed. pp. 313.
Chemical Abstracts, vol. 16, No. 21, May 25, 1992, Abstract No. 211129a.
Broekaert et al., Biochem, vol. 31:4308–4314, 1992.
Broekaert et al., Science, vol. 245:1100–1102, Sep. 8, 1989.
Collard et al., The Cytokines Facts Book, Academic Press, London, pp. 31, 1994.
Schulz et al., Principles of Protein Structure, Springer–Verlag, New York, pp. 14–16, 1979.

* cited by examiner

Primary Examiner—Elizabeth C. Kemmerer
(74) Attorney, Agent, or Firm—Hale and Dorr LLP

(57) ABSTRACT

Biocidal proteins capable of isolation from seeds have been characterized. The proteins have an amino acid sequence containing the common cysteine/glycine domain of Chitin-binding Plant Proteins but show substantially better activity against pathogenic fungi, a higher ratio of basic amino acids to acidic amino acids, and/or antifungal activity which results in increased hyphal branching. Antimicrobial proteins isolated from Amaranthus, Capsicum, Briza and related species are provided. The proteins show a wide range of antifungal activity and are active against Gram-positive bacteria. DNA encoding the proteins may be isolated and incorporated into vectors. Plants may be transformed with this DNA. The proteins find agricultural or pharmaceutical application as antifungal or antibacterial agents. Transgenic plants expressing the protein will show increased disease resistance.

8 Claims, 17 Drawing Sheets

FIG. 2A1
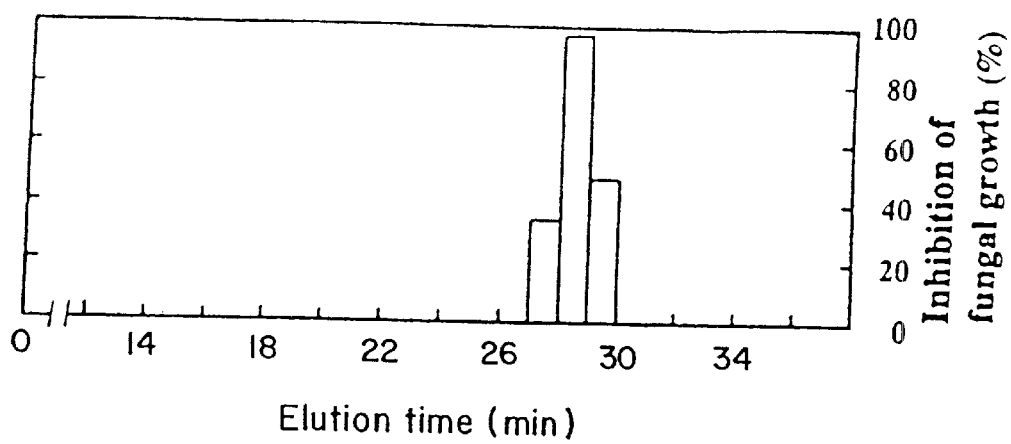
FIG. 2A2
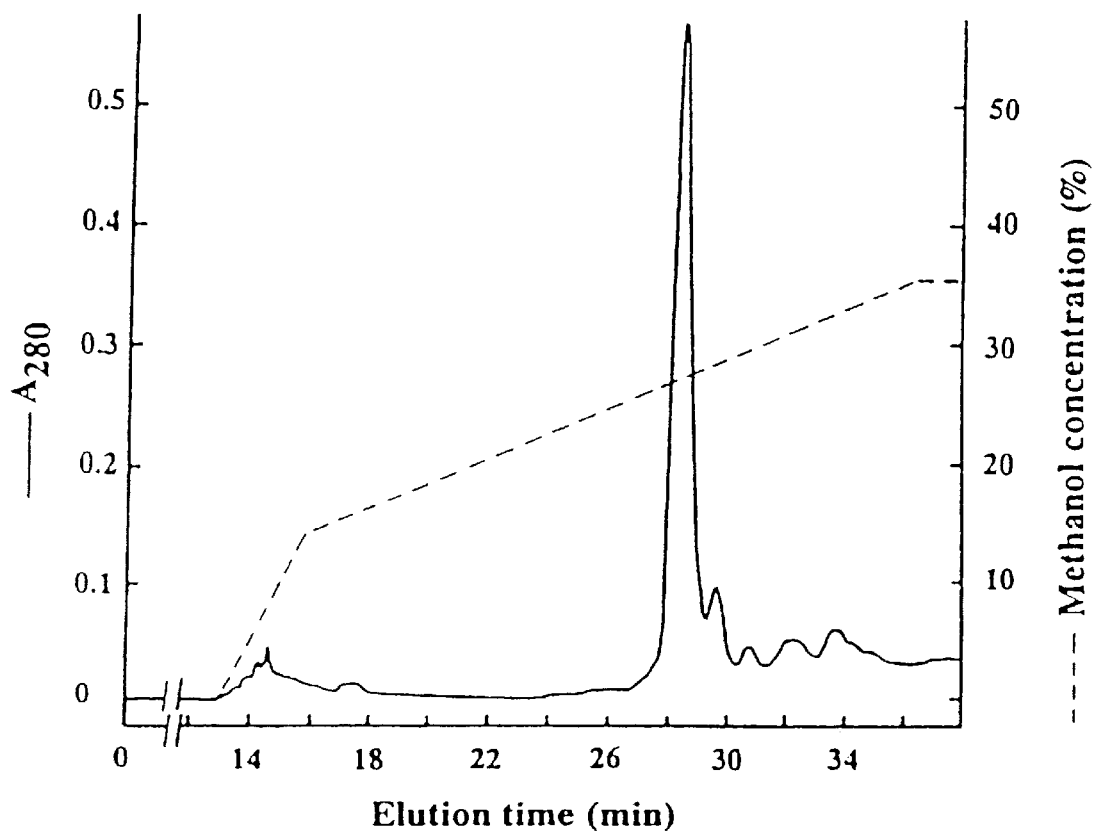

FIG. 2B1
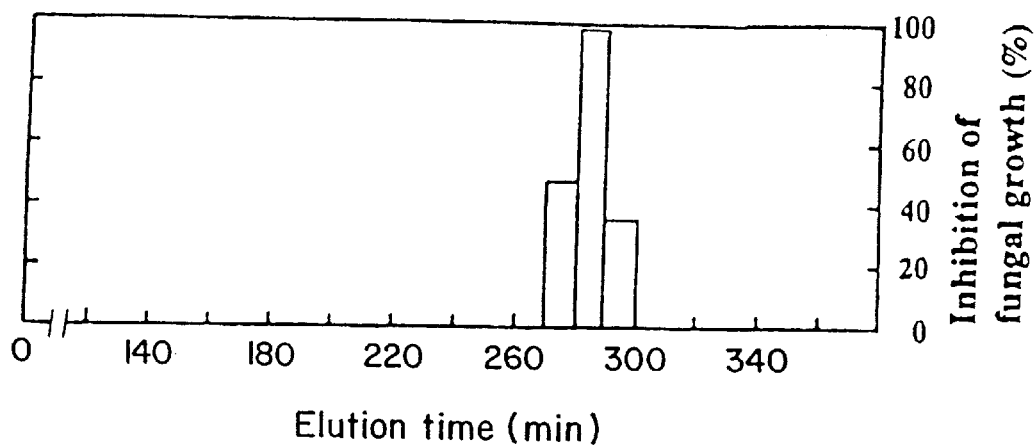
FIG. 2B2
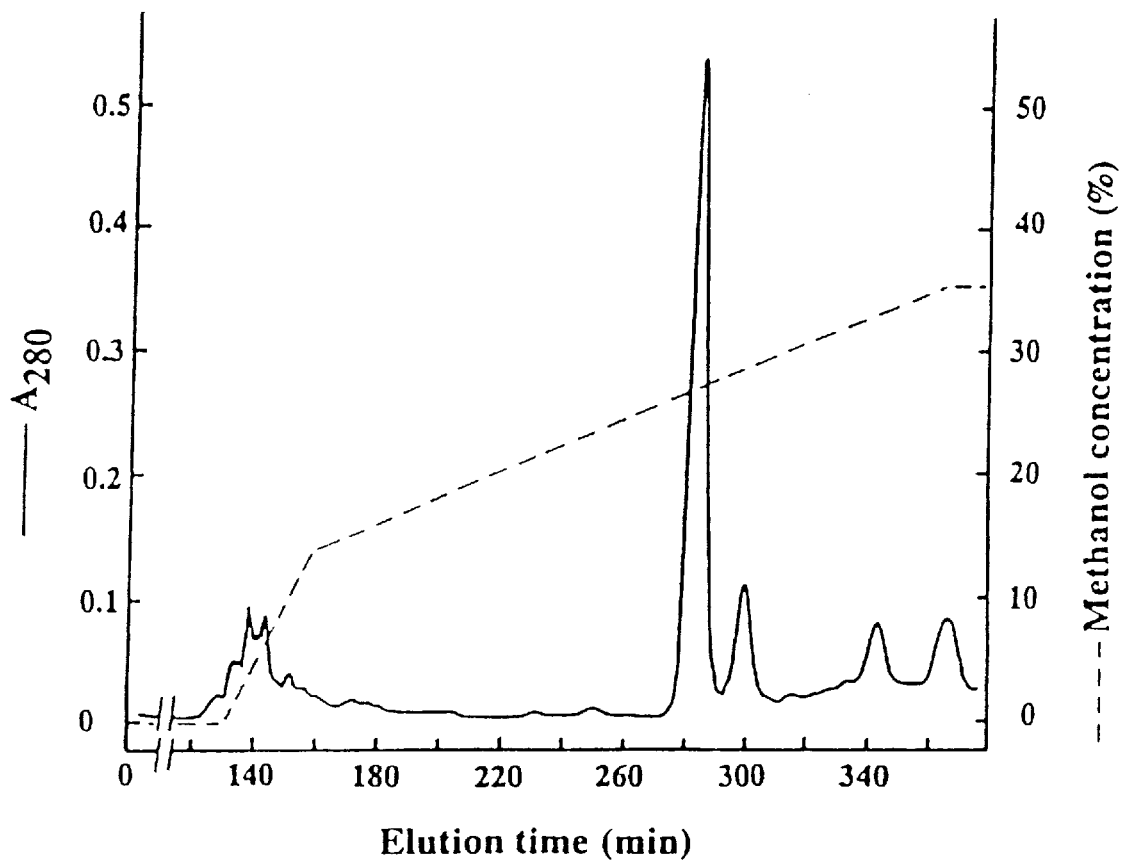

FIG.3A

```
Ac-AMP1   V G E C V R G R C P S G M C C S Q F G Y C G K G P K Y C G
Ac-AMP2   V G E C V R G R C P S G M C C S Q F G Y C G K G P K Y C G R
Ar-AMP1   A G E C V Q G R C P S G M C C S Q F G Y C G R G P K Y C G R
```

FIG.3B

```
To chitinase   * E Q C G S Q A G G A R C A S G L C C S K F G W C G N T N D Y C G P G * N C Q S * Q C P G G
Be chitinase   * E Q C G r Q A G G A l C P g G n C C S q F G W C G s T t D Y C G P G * * C Q S * Q C * G G
Hevein         * E Q C G r Q A G G K l C P n n L C C S q W G W C G s T d E Y C s P d h N C Q S * N C k d s
Wheat lectin   * q r C G e Q G s n n e C P n n L C C S q Y G Y C G m g g D Y C G K G * * C Q d g a C w t s
Nettle lectin  * q r C G S Q G G G G t C P a l r C C S i W G W C G a S s p Y C
Ac-AMP2        v g e C v r * * * G R C P S G M C C S q F G Y C G k g p k Y C G r
```

FIG. 6

```
1   CAAAAAAAAAAAAAAGTCAAGAGTATTAATTAGGTGAGAAAAAATGGTGAACATGAAG
                                                  M  V  N  M  K

61  TGTGTTGCATTGATAGTTATAGTTATGATGGCGTTTATGATGGTGGATCCATCAATGGGA
    C  V  A  L  I  V  I  V  M  M  A  F  M  M  V  D  P  S  M  G

121 GTGGGAGAGAATGTGTGAGAGGACGTTGCCCAAGTGGGATGTGTTGCAGTTGGGTAC
    V  G  E  E  C  V  R  G  R  C  P  S  G  M  C  C  S  Q  F  G  Y

181 TGTGGTAAAGGCCCAAAGTACTGTGGCCGTGCCAGTACTACTGTGGATCACCAAGCTGAT
    C  G  K  G  P  K  Y  C  G  R  A  S  T  T  V  D  H  Q  A  D

241 GTTGCTGCCACCAAAACTGCCAAGAATCCTACCGATGCTAAACTTGCTGGTGCTGGTAGT
    V  A  A  T  K  T  A  K  N  P  T  D  A  K  L  A  G  A  G  S

301 CCATGAAAGTAGTAGCTAGGTTCACGTTGGATTACCAAGCCCGTGCCAGTACTACTG
    P  *

361 TGGCCCGTGCCAGTACTAATGTTCTCTTATATGTCTGAAATAAGCTCCTATATAAATACTA

421 GTATCTTGATGTAATGGAGTATTTCATTTTGTTTTATTGAGTTATGATCGTGACTTC

481 CTTGTGTTGGTTTAACTTGTATATTGTAATGCATCTTAAATGCTCTCAAATAATTTGA

541 TGTATTAAACACTTGTTTTGTTTTTAATACATACTAAGTGCTCTGTAAATTC
```

<--------- N-terminal sequence --------->

<--------- Peptide 1 --------->

<--------- Peptide 2 --------->

FIG. 13

( CAA ) GAG CAA TGC GGA AAC CAA GCT GGA GGA AGA GCT TGC GCT AAC AGA CTT

TGC TGC TCT CAA TAC GGA TAC TGC GGA TCT ACT AGA GCT TAC TGC GGA GTT

GGA TGC CAA TCT AAC TGC GGA AGA

FIG. 12

| | | | | | | | | | | | | |
|---|---|---|---|---|---|---|---|---|---|---|---|---|
| Bm-AMPI | | C | S | S | - | - | H | N | P | C | P | R H | Q C C S K Y G Y C G | L G S D Y C G L G | - - | C R G G | P C D | R |
| Ca-AMPI | (Q) | E | Q | C | G | N | Q | A | G | G | R | A C A N R | L C C S Q Y G Y C G S | T R A Y C G V G | - - | C Q S | N C G | R |
| Ac-AMP2 | V | G | E | C | V | R | - | - | G | R | - | C P S G M | C C S Q F G Y C G K | G P K Y C G R | | | | |
| To chit | | E | Q | C | G | S | Q | A | G | G | A | R C A S G | L C C S K F G W C G N | T N D Y C G P G | - N | C Q S | Q C | P G G |
| Be chit | | E | Q | C | G | R | Q | A | G | G | A | L C P G | N C C S Q F G W C G S | T T D Y C G P G | - - | C Q S | Q C | G G |
| Hevein | | E | Q | C | G | R | Q | A | G | G | K | L C P N | N C C S Q W G W C G S | T D E Y C S P D H N | C Q S | N C | K D S |
| Wh lect | | Q | R | C | G | E | Q | G | S | N | N | E C P N | L C C S Q Y G Y C G M | G G D Y C G K G | - - | C Q S | N C | - G G |
| Nettle lect | | Q | R | C | G | S | Q | G | G | G | G | T C P A L R | C C S I W G W C G | M G G D Y C G | S S P Y C | C Q D G A C W T S |

FIG. 16

Bm-AMP1    C S S H N P C P R H Q C C S K Y G Y C G L G S D Y C G L G C R G G P C D R
                       H                                 N

FIG. 17

TGC TCT TCT CAC AAC CCG TGC CCG AGA CAC CAA TGC TGC
TCT AAG TAC GGA TAC TGC GGA CTT GGA TCT GAC TAC TGC
GGA CTT GGA TGC AGA GGA GGA CCG TGC GAC AGA

BIOCIDAL PROTEINS

This is a continuation of application Ser. No. 08/777,113 filed on Dec. 30, 1996, now U.S. Pat. No. 5,986,176, which is a division of application Ser. No. 08/451,566 filed May 26, 1995, now U.S. Pat. No. 5,691,199, which is a division of application Ser. No. 08/149,839 filed Nov. 10, 1993, now U.S. Pat. No. 5,514,779, which is a continuation-in-part of application Ser. No. 08/002,842 filed Jan. 14, 1993 now abandoned, which is a continuation-in-part of PCT/GB92/00999 filed Jun. 3, 1992.

BACKGROUND OF THE INVENTION

This invention relates to biocidal proteins, processes for their manufacture and use, and DNA sequences encoding them. In particular it relates to a class of antimicrobial proteins including protein capable of being isolated from seeds of Amaranthus, Capsicum or Briza.

In this context, antimicrobial proteins are defined as proteins possessing at least one of the following activities: antifungal activity (which may include anti-yeast activity); antibacterial activity. Activity includes a range of antagonistic effects such as partial inhibition or death. Such proteins may be oligomeric or may be single peptide subunits.

*Amaranthus caudatus* (amaranth) belongs to a large family, the Amaranthaceae, of herbs and shrubs which grow widely in tropical, sub-tropical and temperate regions. Amaranth is an ancient food crop of the Americas, and is still cultivated for grain production in parts of Central and South America, Asia and Africa. Amaranth seeds can be popped, toasted, cooked for gruel, milled into flour or made into flat breads, and have a particularly high nutritive value (Betschart et al, 1981, J Food Sci, 46:1181–1187; Pedersen et al, 1987,Plant Food Hum Nutr,36:309–324). Amaranth is also cultivated world-wide as a garden ornamental.

The genus Capsicum comprises fifty species and includes many important vegetable species which are grown throughout the world (for example, green and red peppers, chillies, paprika and cayenne pepper). As well as these widely cultivated examples, Capsicum also includes a number of species which are grown for their colourful but inedible fruits.

The genus Briza comprises many ornamental grasses and belongs to the Gramineae family. The genus is closely related to grass species found in high-grade temperate pasture, such as rye grass.

Plants produce a wide array of antifungal compounds to combat potential invaders and over the last ten years it has become clear that proteins with antifungal activity form an important part of these defences. Several classes of proteins have been described including thionins, beta-1,3-glucanases, ribosome-inactivating proteins and chitinases. This last group of enzymes falls into a wider class hereafter referred to as the "Chitin binding Plant Proteins".

Chitin (poly-β-1,4-N-acetyl-D-glucosamine) is a polysaccharide occurring in the cell wall of fungi and in the exoskeleton of invertebrates. Although plants do not contain chitin or chitin-like structures, proteins exhibiting strong affinity to this polysaccharide have been isolated from different plant sources (Raikhel and Broekaert, 1991, in: Verma, ed, Control of plant gene expression, in press).

Basic chitinases have been isolated from bean (Boller et al, 1983, Planta, 157:22–31), wheat (Molano et al, 1979, J Biol Chem, 254:4901–4907), tobacco (Shinshi et al, 1987, Proc Nat Acad Sci USA,84:89–93) and other plants. The other known Chitin-binding Plant Proteins have no defined catalytic activity and have thus been described solely on their lectin activity. These include chitin-binding lectins from wheat (Rice and Etzler, 1974, Biochem Biophys Res Comm, 59:414–419), barley (Peumans et al, 1982, Biochem J, 203:239–143), rice (Tsuda, 1979, J Biochem, 86:1451–1461) and stinging nettle (Peumans et al, 1983, FEBS Lett, 177:99–103) plus a small protein from the latex of the rubber tree, called hevein (van Parijs et al, 1991, Planta,183:258–264).

Thus the Chitin-binding Plant Proteins (as herein defined) are a protein group consisting of chitinases, chitin-binding lectins and hevein. All these proteins contain a conserved cysteine-glycine rich domain (for a review see Raikel and Broekaert, 1991, in Control of plant gene expression, Verma DP (ed), Telford Press). This common region may confer the chitin-binding activity. The domain is 40–43 amino acids in length and is either repeated twice (nettle lectin), four-fold (in wheat, barley and rice lectins) or fused to an unrelated domain (in basic chitinases and prohevein). Hevein itself is 43 amino acids in length and comprises essentially just this conserved domain (Broekaert et al, 1990, Proc Nat Acad Sci USA, 87:7633–7637). A cDNA clone (HEV1) encoding hevein has been isolated (Raikhel and Broekaert, U.S. Pat. No. 5,187,262, published Feb. 16, 1993). FIG. 15 shows the common cysteine/glycine-rich domain found in the following Chitin-binding Plant Proteins: tobacco shitinase, bean chitinase, hevein, wheat lectin, nettle lectin. Sequence identities and conserved changes are boxed (conserved changes are considered as substitutions within the amino acid homology groups Phe/Trp/Tyr, Met/Ile/Leu/Val (SEQ ID NO: 20), Arg/Lys/His/, Glu/Asp, Asn/Gln, Ser/Thr, and Pro/Ala/Gly; gaps introduced for maximum alignment are represented by dashes). The central region of nine amino acid residues is a particularly well conserved feature of the domain and has the sequence (SEQ ID NO:. 21):

```
cycsteine-cycsteine-(serine or threonine)-
1         2          3

(any residue)-(tryptophan, tyrosine or
4              5 phenylalanine)-glycine-(tryptophan,
               6        7 tyrosine or phenylalanine)- cysteine-glycine.
8         9
```

Around this core region, the central cysteine motif of the cysteine/glycine rich domain is also absolutely conserved and has the sequence (SEQ ID NO: 22): cysteine-(four amino acids)-cysteine-cysteine-(five amino acids)-cysteine-(six amino acids)-cysteine.

The exact physiological role of these proteins remains uncertain, but a defence-related function has been suggested. The Chitin-binding Plant Proteins have been found to affect the growth of certain organisms that contain chitin (fungi or insects). However there are differences in the specificity of the proteins. For example, the wheat/barley/rice-type lectins are toxic to weevils, but are inactive to fungi in vitro (Murdock et al, 1990, Phytochem, 29: 85–89). On the other hand, hevein and the chitinases have been found to be inhibitory to the growth of certain pathogenic fungi in vitro (Van Parijs et al, 1991 Planta, 183: 258–264 ; Broekaert et al, 1988, Physiol Mol Plant Path, 33: 319–331). The HEV1 protein can be used to inhibit the growth of fungi (Raikhel and Broekaert, U.S. Pat. No. 5,187,262, published Feb. 16, 1993). Nettle lectin has also been shown to exert antifungal activity in vitro and at a level 2- to 5-fold greater than hevein (Broekaert et al, 1989, Science, 245: 1100–1102). It is not established whether or not the observed effects on fungi or insects are related to the chitin-binding activity of these proteins.

Application of Chitin-binding Plant Proteins, especially chitinases, in the protection of plants against fungal disease has been reported, and the potential usefulness of these proteins to engineer resistance in plants has been described (for example, Pioneer Hi Bred's European Patent Application 502718). In U.S. Pat. No. 4,940,840 (DNA Plant Technology Corporation), tobacco plants expressing a chitinase gene from the bacterium *Serratia marcescens* appear to be less sensitive to the fungus *Alternaria longipes*. European Patent Application Number 418695 (Ciba Geigy) describes the use of regulatory DNA sequences from tobacco chitinase gene to drive expression of introduced genes producing transgenic plants with improved resistance to pathogens. Patent Application Number WO9007001 (Du Pont de Nemours Company) describes production of transgenic plants which over-express a chitinase gene giving improved resistance to fungal pathogens.

SUMMARY OF THE INVENTION

We have now identified a new class of potent antimicrobial proteins.

According to the present invention, there is provided an isolated antimicrobial protein having an amino acid sequence containing the common cysteine/glycine domain of Chitin-binding Plant Proteins and having one or more of the following properties:

substantially better activity against plant pathogenic fungi than that of the Chitin-binding Plant Proteins;

a higher ratio of basic amino acids to acidic amino acids than the Chitin-binding Plant Proteins;

activity against plant pathogenic fungi resulting in hyphal branching.

In particular there is provided an antimicrobial protein capable of being isolated from seeds of Amaranthus, an antimicrobial protein capable of being isolated from seeds of Capsicum, and an antimicrobial protein capable of being isolated from seeds of Briza. Such antimicrobial proteins may also be isolated from the seeds of both related and unrelated species (including Catapodium, Baptisia, microsensis, Delphinium), or may be produced or synthesized by any suitable method.

We have isolated two antimicrobial proteins from seeds of *Amaranthus caudatus* (amaranth). The two protein factors are hereafter called Ac-AMP1 (*Amaranthus caudatus*— Antimicrobial Protein 1) and Ac-AMP2 (*Amaranthus caudatus*—Antimicrobial Protein 2) respectively. Both are dimeric proteins, composed of two identical 3 kDa subunits. Both proteins are highly basic and have pI values above 10. Proteins with similar antifungal activity have been extracted from the seed of several closely related species, including *Amaranthus paniculatus, Amaranthus retroflexus, Amaranthus lividus* and *Gomphrena globossa*.

The amino acid sequence of Ac-AMP1 (29 residues) is identical to that of Ac-AMP2 (30 residues), except that the latter has one additional residue at the carboxyl-terminus. A similar antimicrobial protein, hereafter called Ar-AMP1, has been isolated from *Amaranthus retroflexus* seed. The amino acid sequence of Ar-AMP1 (31 residues) is almost identical to that of Ac-AMP2, having one additional residue at the carboxyl-terminus plus one conservative change and two real amino acid changes.

The amino acid sequences of Ac-AMP1 and Ac-AMP2 are highly homologous to those of the Chitin-binding Plant Proteins and essentially comprise the cysteine/glycine-rich domain identified in chitin-binding lectins. Moreover, Ac-AMP1 and Ac-AMP2 bind to chitin and can be desorbed at low pH (a property shared by chitinases and lectins). However, when compared to the regular 40–43 amino acid cysteine/glycine-rich domains found in the Chitin-binding Plant Proteins, the Ac-AMPs distinguish themselves by several features. These include a higher abundance of basic amino acids, the presence of an additional amino-terminal residue, the occurrence of a gap of four amino acids at position 6 to 9, and the lack of a carboxyl-terminal portion of 10–12 residues.

Both Ac-AMP1 and Ac-AMP2 show surprisingly high activity: they inhibit the growth of a variety of plant pathogenic fungi at much lower doses than the antifungal Chitin-binding.Plant Proteins. The antifungal effect of the novel proteins is antagonized by $Ca^{2+}$. On five tested fungi, the antifungal activity of Ar-AMP1 is indistinguishable from that of the Ac-AMPs.

Some Chitin-binding Plant Proteins are known to have an effect against insects which possess an exoskeleton comprising chitin. The sequence similarity between the Ac-AMPs and the Chitin-binding Plant Proteins implies that the Ac-AMPs may also possess insecticidal properties.

We have also purified a new antimicrobial protein from seeds of *Capsicum annuum*, hereafter called Ca-AMP1 (*Capsicum annuum* antimicrobial protein 1). The protein shares the common cysteine/glycine domain of the Chitin-binding Plant Proteins, but is unique as it possesses very potent and broad spectrum antifungal activity which is at least an order of magnitude greater than hevein or nettle lectin. So despite the conserved nature of these protein sequences (for example, the amino acid sequence for Ca-AMP1 is 65% identical to hevein), the Capsicum protein is markedly improved in the potency and spectrum of its antifungal activity. Indeed, it is remarkable that Ca-AMP1 and hevein are so similar in size and amino acid sequence, but differ so dramatically in their levels and spectrum of activity.

We have also purified a new antimicrobial protein from seeds of *Briza maxima*, hereafter called Bm-AMP1 (*Briza maxima* antimicrobial protein 1). The protein shares the common cysteine/glycine domain of the Chitin-binding Plant Proteins, but is unique as it possesses very potent and broad spectrum antifungal activity. So despite the conserved nature of these protein sequences, the Briza protein is markedly improved in the potency and spectrum of its antifungal activity. The amino acid sequence for Bm-AMP1 is 45% identical to Ca-AMP1 but only 35% to hevein.

The antifungal activity of Ca-AMP1 and of Bm-AMP1 is similar to that of the Amaranthus (Ac-AMP) proteins discussed above: all these proteins are substantially more basic than hevein or the nettle lectin which may account for the difference in activity.

We have found that possession of an overall basic profile contributes to the effectiveness of an antifungal protein. For example, in different classes of antifungal proteins isolated from Mirabilis and Raphanus it is always the more basic homologue that is the most active (Terras et al, 1992, J Biol Chem, 267: 15301–15309 ; Cammue et al, 1992, J Biol Chem, 267: 2228–2233). The basic amino acids are lysine (K), arginine (R) and histidine (H); the acidic amino acids are aspartate (D) and glutamate (E). Although the sequence of the Capsicum (Ca-AMP1) protein is very similar to that of hevein, the ratio of basic to acidic amino acids is 4:1 for Ca-AMP1 but 4:5 (ie much lower) for hevein. In Ac-AMP1, the ratio of basic to acidic amino acids is 4:1 and in Ac-AMP2 and Ar-AMP1 the ratio is 5:1. The ratio of basic to acidic amino acids is 3:1 for Bm-AMP1. It may be that the basic nature of Ca-AMP1, the Ac-AMPs, Ar-AMP1 and Bm-AMP1 accounts for their improved potency. It is likely therefore that increasing the basic nature of certain Chitin-binding Plant Proteins (such as hevein) using site-directed mutagenesis would potentiate any antifungal activity, particularly if substitutions were made at positions where there are basic amino acids in the Capsicum (Ca-AMP1) protein (such as replacement of the aspartic acid at position 28 in hevein) or at positions where there are basic amino acids in the Briza (Bm-AMP1) protein. By adapting the structure of certain Chitin-binding Plant Proteins, it is therefore possible to create new, more potent antimicrobial proteins of the invention.

During the course of screening many different plant species it has become evident that the protein class of the invention is fairly common in plant seeds. It is possible to distinguish the proteins' antifungal activity on the basis of the unexpected morphological effect they produce: severe branching of hyphae occurs in partially inhibited germinating fungal spores. This is particularly evident when using *Fusarium culmorum*. The nature of the inhibition may also be characterized by the fact that it is very sensitive to the concentration of cations used in the assay.

Despite the similarities in sequence, activity (level and effect) and basicity between the Capsicum protein (Ca-AMP1) and the Amaranthus proteins (Ac-AMPS), there are certain differences in their primary and tertiary structures. FIG. 15 shows that the sequence of Ca-AMP1 contains at least forty-two amino acid residues. However, Ac-AMP2 is a shorter peptide: the full Ac-AMP2 sequence contains only thirty amino acid residues. Furthermore, the extra sequence of Ca-AMP1 contains two additional cysteine residues which are not found in the Ac-AMP2 protein. As cysteines are involved in internal linkages within proteins, it is probable that the tertiary structures of Ca-AMP1 and Ac-AMP2 are different.

Bm-AMP1 resembles Ca-AMP1 with respect to its total number of amino acids and its number of cysteine residues. It is probable that Bm-AMP1 and Ca-AMP1 share considerable homology at both the secondary and tertiary level. It is also probable that, like Ca-AMP1, Bm-AMP1 differs from Ac-AMP2 in its tertiary structure due in part to the two additional cysteine residues found in Bm-AMP1.

The invention further provides an isolated DNA sequence coding for a protein of the invention, and a vector containing said sequence. The DNA may be cloned or transformed into a biological system allowing expression of the encoded protein.

There is further provided a plant transformed with recombinant DNA encoding an antimicrobial protein according to the invention.

There is also provided a process of combating fungi or bacteria, whereby they are exposed to the protein according to the invention.

The Ac-AMP, Ar-AMP1, Ca-AMP1 and Bm-AMP1 proteins show a wide range of antifungal activity, and are also active against Gram-positive bacteria. Each protein is useful as a fungicide or an antibiotic, for agricultural or pharmaceutical applications. Exposure of a plant pathogen to an antimicrobial protein may be achieved by expression of the protein within a micro-organism which is applied to a plant or the soil in which a plant grows. The proteins may also be used to combat fungal or bacterial disease by application of the protein to plant parts using standard agricultural techniques (eg spraying). The proteins may also be used to combat fungal or bacterial disease by expression within plant bodies, either during the life of the plant or for post-harvest crop protection. The protein may also be used as a fungicide to treat mammalian infections.

The antimicrobial protein may be isolated and purified from appropriate seeds, synthesized artificially from its known amino acid sequence, or produced within a suitable micro-organism by expression of recombinant DNA. The proteins may also be expressed within a transgenic plant.

Knowledge of the primary structure enables manufacture of the antimicrobial protein, or parts thereof, by chemical synthesis using a standard peptide synthesizer. It also enables production of DNA constructs encoding the antimicrobial protein. The DNA sequence may be predicted from the known amino acid sequence or the sequence may be isolated from plant-derived DNA libraries.

Oligonucleotide probes may be derived from the known amino acid sequence and used to screen a cDNA library for cDNA clones encoding some or all of the protein. These same oligonucleotide probes or cDNA clones may be used to isolate the actual antimicrobial protein gene(s) by screening genomic DNA libraries. Such genomic clones may include control sequences operating in the plant genome. Thus it is also possible to isolate promoter sequences which may be used to drive expression of the antimicrobial (or other) proteins. These promoters may be particularly responsive to environmental conditions (such as the presence of a fungal pathogen), and may be used to drive expression of any target gene.

cDNA encoding the Ac-AMPs has been isolated and sequenced. The cDNA encoding Ac-AMP2 has been identified. It encodes an 86-amino acid pre-protein and a 25-amino acid carboxy-terminal extension. The structure of this preprotein differs from all precursors of Chitin-binding Plant Proteins. The cDNA encoding Ac-AMP1 has been identified as a post-translational cleavage product of Ac-AMP2.

DNA encoding the antimicrobial protein (which may be a cDNA clone, a genomic DNA clone or DNA manufactured using a standard nucleic acid synthesizer) can then be cloned into a biological system which allows expression of the protein or a part of the protein. The DNA may be placed under the control of a constitutive or inducible promoter. Examples of inducible systems include pathogen induced expression and chemical induction. Hence the protein can be produced in a suitable micro-organism or cultured cell, extracted and isolated for use. Suitable micro-organisms include *Escherichia coli,* Pseudomonas and yeast. Suitable cells include cultured insect cells and cultured mammalian cells. The genetic material can also be cloned into a virus or bacteriophage. The DNA can also be transformed by known methods into any plant species, so that the antimicrobial protein is expressed within the plant.

Plant cells according to the invention may be transformed with constructs of the invention according to a variety of known methods (Agrobacterium Ti plasmids, electroporation, microinjection, microprojectile gun, etc). The transformed cells may then in suitable cases be regenerated into whole plants in which the new nuclear material is stably incorporated into the genome. Both transformed monocotyledonous and dicotyledonous plants may be obtained in this way, although the latter are usually more easy to regenerate.

BRIEF DESCRIPTION OF THE DRAWINGS

Examples of genetically modified plants which may be produced include field crops, cereals, fruit and vegetables such as: canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

The invention may be further understood by reference to the drawings, in which:

FIGS. 2A1 and 2A2 show the HPLC profile of purified Ac-AMP1.

FIGS. 2B1 and 2b2 show the HPLC profile of purified Ac-AMP2.

FIG. 3A shows the amino acid sequences of Ac-AMP1, Ac-AMP2 and Ar-AMP1(SEQ ID NO: 5 to SEQ ID NO: 7, respectively).

FIG. 3B shows the alignement of amino acid sequences from tobacco chitinase, bean chitinase, hevein, wheat lectin, nettle lectin (SEQ ID NO: 8 to SEQ ID NO: 12, respectively), and Ac-AMP2 (SEQ ID NO: 6).

FIG. 6 shows the nucleotide sequence and deduced amono acid sequence of a cDNA clone encloding Ac-AMP2 (SEQ ID NO: 13 and SEQ ID NO: 14, respectively).

FIG. 11 shows the amono acid sequence of Ca-AMP1 (SEQ ID NO: 15).

FIG. 12 shows the alignment of the amino acid sequence of Bm-AMP1 (SEQ ID NO: 16), Ca-AMP1 (SEQ ID NO: 15), Ac-AMP2 (SEQ ID NO: 6) and a number of chitin-binding lectins (SEQ ID NO: 8–12, respectively).

FIG. 13 shows one possible predicted DNA sequence for the Ca-AMP1 gene (SEQ ID NO: 17).

FIG. 16 shows the amino acid sequence of Bm-AMP1 (SEQ ID NO: 16 and SEQ ID NO: 18, respectively).

FIG. 17 shows one possible predicted DNA sequence for Bm-AMP1 (SEQ ID NO: 19).

DESCRIPTION OF PREFERRED EMBODIMENTS

Figure 1A:
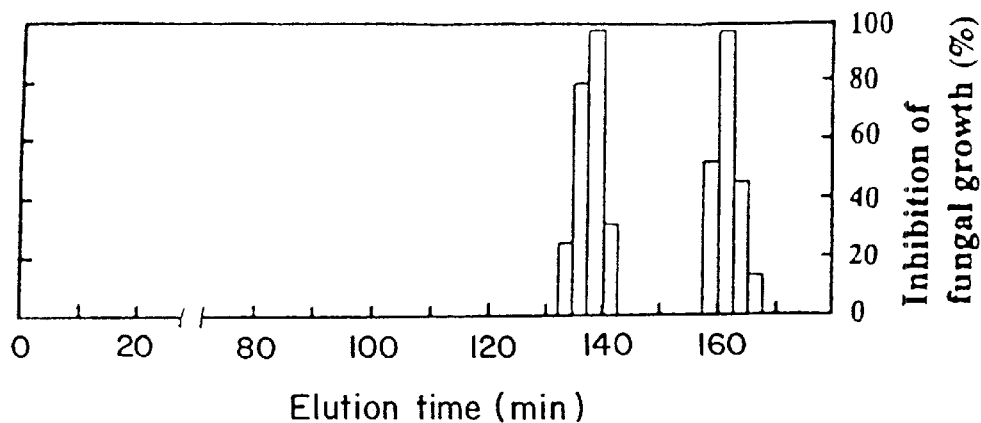
FIGS. 1A and 1B show the cation exchange chromatogram for the antifungal proteins and the associated graph of fungal growth inhibition.

The following examples illustrate the invention.

EXAMPLE 1

Antifungal and Antibacterial Activity Assays

Antifungal activity was measured by microspectrophotometry as previously described (Broekaert, 1990, FEMS Microbiol Lett, 69:55–60). Routinely, tests were performed with 20 μl of a (filter-sterilized) test solution and 80 μl of a fungal spore suspension ($2\times10^4$ spores/ml) or mycelium fragments in either half strength potato dextrose broth (medium A) or half strength potato dextrose broth with $CaCl_2$ and KCl added to final concentrations of 1 mM and 50 mM respectively (medium B). For experiments on the antagonistic effect of cations, a synthetic growth medium was used instead of Potato Dextrose Broth. The synthetic growth medium consisted of $K_2HPO_4$ (2.5 mM), $MgSO_4$ (50 μM), $CaCl_2$ (50 μM), $FeSO_4$ (5 μM), $CoCl_2$ (0.1 μM), $CuSO_4$ (0.1 μM), $Na_2MoO_4$ (2 μM), $H_3BO_3$ (0.5 μM), KI (0.1 μM), $ZnSO_4$ (0.5 μM), $MnSO_4$ (0.1 μM), glucose (10 g/l), asparagine (1 g/l), methionine (20 mg/l), myo-inositol (2 mg/l), biotin (0.2 mg/l), thiamine-HCl (1 mg/l), and pyridoxine-HCl (0.2 mg/l). Control microcultures contained 20 μl of sterile distilled water and 80 μl of the fungal spore suspension.

Unless otherwise stated the test organism was *Fusarium culmorum* (strain IMI 180420) and incubation was carried out at 25° C. for 48 hours. Percent growth inhibition is defined as 100 times the ratio of the corrected absorbance of the control microculture minus the corrected absorbance of the test microculture over the corrected absorbance at 595 nm of the control microculture. The corrected absorbance values equal the absorbance at 595 nm of the culture measured after 48 hours minus the absorbance at 595 nm measured after 30 min. Values of growth inhibition lower than 15% are not indicated on the chromatograms. The antifungal activity (units per ml) is calculated as 50 times the dilution factor of a test solution at which 50% growth inhibition is obtained under the given assay conditions.

Antibacterial activity was measured microspectrophotometrically as follows. A bacterial suspension was prepared by inoculating soft nutrient agarose (tryptone, 10 g/l; Seaplaque agarose (FMC), 5 g/l) and kept at 37° C. to prevent solidification. Aliquots (80 μl) of the bacterial suspension ($10^5$ colony forming units per ml) were added to filter-sterilized samples (20 μl) in flat-bottom 96-well microplates. The absorbance at 595 nm of the culture was measured with the aid of a microplate reader after 30 minutes and 24 hours of incubation at 28° C. Percent growth inhibition was calculated as described above for the antifungal activity assay.

EXAMPLE 2

Extraction of Basic Heat-stable Proteins From Seeds 2.1 *Amaranthus caudatus* Seeds Ammonium sulphate fractionation of proteins precipitating in the interval of 30 to 75% relative saturation was followed by isolation of the basic protein fraction (pI>9) by passage over a Q-Sepharose (Pharmacia) anion exchange column equilibrated at pH 9. The detailed methods are described below.

One kg of *A. caudatus* seeds (obtained from Gonthier, Wanze, Belgium) was ground in a coffee mill and the resulting meal was extracted for 2 hours at 4° C. with 3 liters of an ice-cold extraction buffer containing 10 mM $NaH_2PO_4$, 15 mM $Na_2HPO_4$, 100 mM KCl, 2 mM EDTA, 2 mM thiourea, 1 mM PMSF and 1 mg/l leupeptin. The homogenate was squeezed through cheesecloth and clarified by centrifugation (5 min at 7,000×g). Solid ammonium sulphate was added to the supernatant to obtain 30% relative saturation and the precipitate formed after standing for 1 hour at room temperature was, removed by centrifugation (10 min at 7,000×g). The supernatant was adjusted to 75% relative ammonium sulphate saturation and the precipitate formed overnight at room temperature collected by centrifugation (30 min at 7,000×g). After redissolving the pellet in 300 ml distilled water, the insoluble material was removed by further centrifugation (20 min at 7,000×g). The clear supernatant was dialyzed extensively against distilled water using benzoylated cellulose tubing (Sigma, St Louis, Mo.) with a molecular weight cut off of 2,000 Da. After dialysis the solution was adjusted to 50 mM Tris-HCl (pH 9) by addition of the ten-fold concentrated buffer, and subsequently passed over a Q-Sepharose Fast Flow (Pharmacia, Uppsala, Sweden) column (12×5 cm) in equilibrium with 50 mM Tris-HCl (pH 9). The proteins passed through the column were dialyzed extensively against 20 maM sodium phosphate buffer (pH 7).

This material represents the basic protein fraction of *A caudatus* seeds. Its chromatographic purification is described in Example 3.

2.2 *Capsicum annuum* or *Briza maxima* Seeds

One kilogramme of *Capsicum annuum* or *Briza maxima* seeds (from Chiltern seeds, Cumbria, UK) were ground in a coffee mill and the resulting meal was extracted for 2 hours at 4° C. with 2 liters of an ice-cold extraction buffer containing 10 mM $NaH_2PO_4$, 15 mM $Na_2HPO_4$, 100 mM KCl, 2 mM EDTA and 1 mM benzamidine. The resulting homogenate was squeezed through cheesecloth and clarified by centrifugation (30 min at 7,000×g). Solid ammonium sulphate was added to the supernatant to obtain 75% relative saturation and the precipitate allowed to form by standing overnight at 4° C. Following centrifugation at 7,000×g for 30 minutes, the precipitate was redissolved in a minimal volume of distilled water and dialyzed extensively against distilled water using benzoylated cellulose tubing (Sigma, St Louis, Mo.). After dialysis the solution was adjusted to 50 mM $NH_4AC$ (pH 9) by addition of the ten-fold concentrated buffer and passed over a Q-Sepharose Fast Flow (Pharmacia, Uppsala, Sweden) column (12×5 cm) equilibrated in 50 mM $NH_4AC$ (pH 9). The protein fraction which passed through the column was adjusted to pH6 with acetic acid.

This material represents the basic (pI>9) protein fraction of the seeds. The fractions were further purified as described in Example 3.

EXAMPLE 3

Purification of Antimicrobial Proteins 3.1 *A caudatus* Seeds

The starting material for the isolation of the *A caudatus* antifungal proteins was the basic protein fraction extracted from the mature seeds as in Example 2.1. These proteins were further separated by cation exchange chromatography, as shown in FIG. 1B.

About 100 mg of the basic protein fraction dissolved in 20 mM sodium phosphate buffer (pH 7) was applied on a S-Sepharose High Performance (Pharmacia) column (10× 1.6 cm) previously equilibrated with the sodium phosphate buffer. The column was eluted at 3 ml/min with a linear gradient of 210 ml form 0 to 150 mM NaCl in 20 mM sodium phosphate buffer (pH 7). The eluate was monitored for protein by online measurement of the absorbance at 280 nm (results shown in FIG. 1B) and collected in 7.5 ml fractions of which 20 µl was tested in the microspectrophotometric antifungal activity assay described in Example 1 (results shown in FIG. 1A).

Figure 1B:
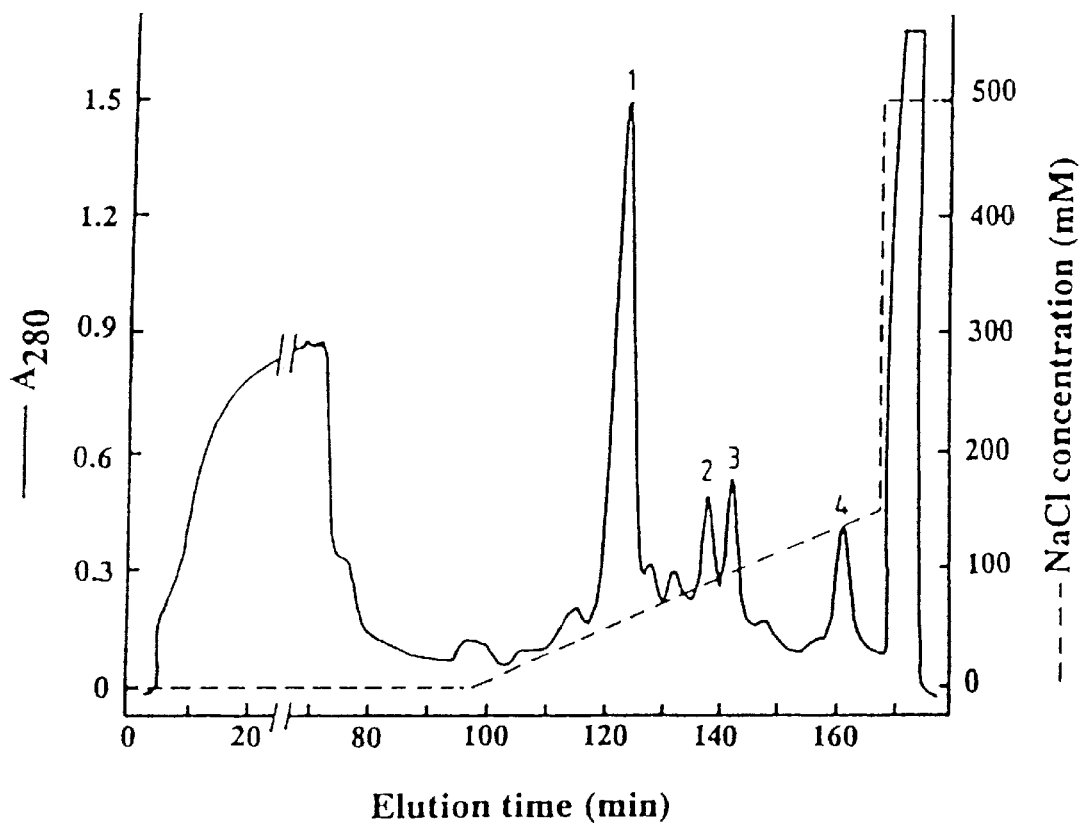

Upon fractionation, the mixture resolved into four distinct peaks (FIG. 1B). The antifungal activity co-eluted with the material from peaks 2 and 4, respectively.

The active fractions were finally purified by reversed-phase chromatography. About 1 mg amounts of peak 2 material (FIG. 2A) and peak 4 material (FIG. 2B) were loaded on a Pep-S (porous silica $C_2/C_{18}$, Pharmacia) column (25×0.93 cm) in equilibrium with 0.1% TFA. The column was eluted at 5 ml/min with the following gradients (solvent B is methanol containing 0.1% TFA): 0–3 min, 0–15% B; 3–23 min, 15–35% B; 23–25 min, 35–100% B. The eluate was monitored for protein by online measurement of the absorption at 280 nm. Five ml fractions of the eluate were collected, vacuum-dried, and finally dissolved in 0.5 ml distilled water of which 10 µl was used in a microspectrophotometric antifungal activity assay.

FIG. 2A and FIG. 2B show the HPLC profiles of purified peak 2 and peak 4 material respectively. The lower panels show monitoring of the eluate for protein by measurement of the absorption at 280 nm. Results of the microspectrophotometric antifungal activity assay are shown in the upper panels.

Both material from peak 2 and from peak 4 yielded well resolved major peaks that co-eluted with the antifungal activity. The active factor purified from peak 2 is called Ac-AMP1 (*Amaranthus caudatus* antifungal protein 1), and that from peak 4 is designated analogously as Ac-AMP2.

3.2 *Capsicum annuum* or *Briza maxima* Seeds

The starting material for the isolation of the *C annuum* or *B maxima* antimicrobial protein was the basic protein fraction extracted from the mature seeds as in Example 2.2. Proteins were further purified by cation exchange chromatography of this extract.

Figure 9A:
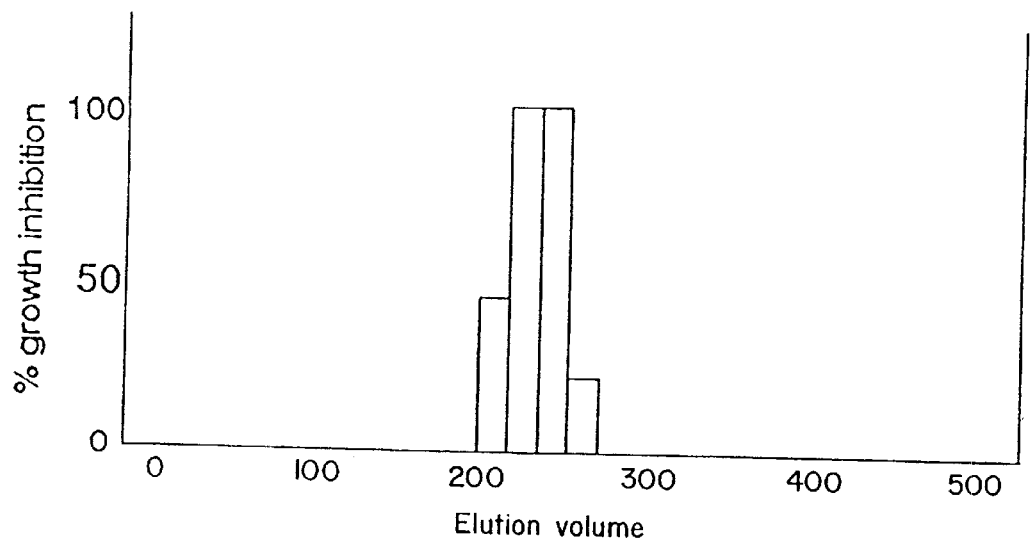
FIG. 9A shows a graph of antifungal activity of Ca-AMP1.
Figure 9B:
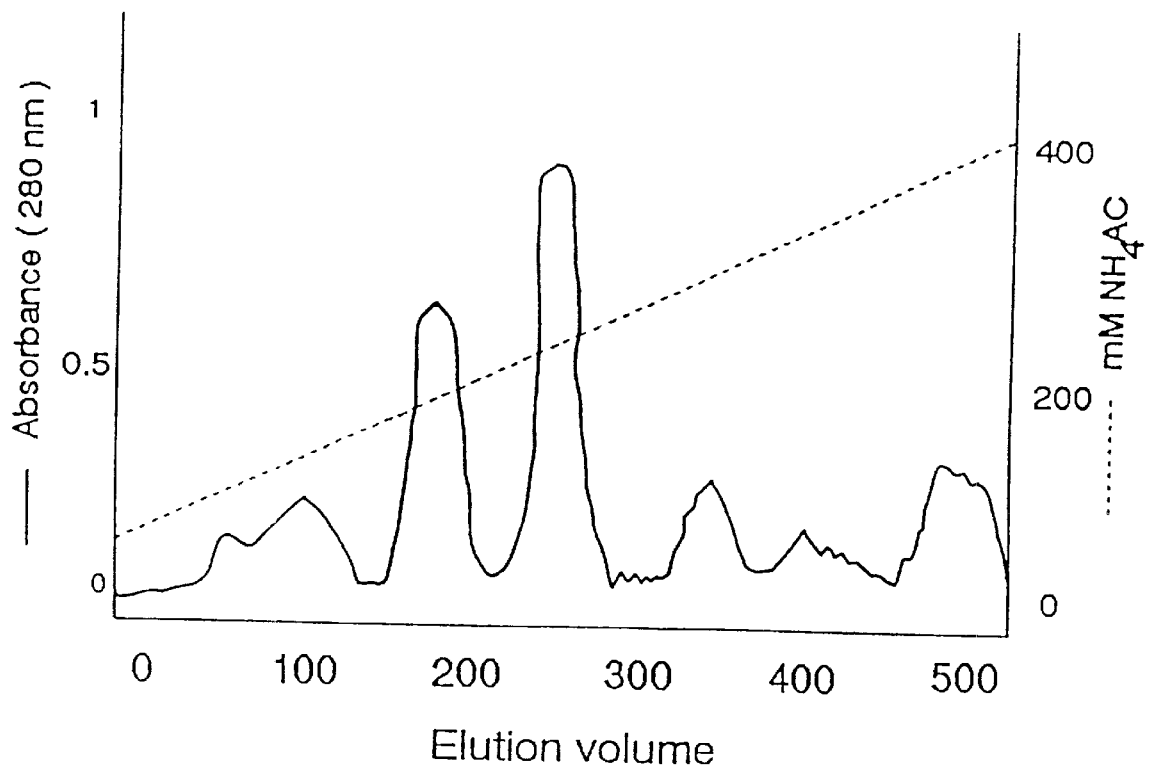
FIG. 9B shows the cation exchange cheomatogram for the purification of Ca-AMP1.
Figure 14A:
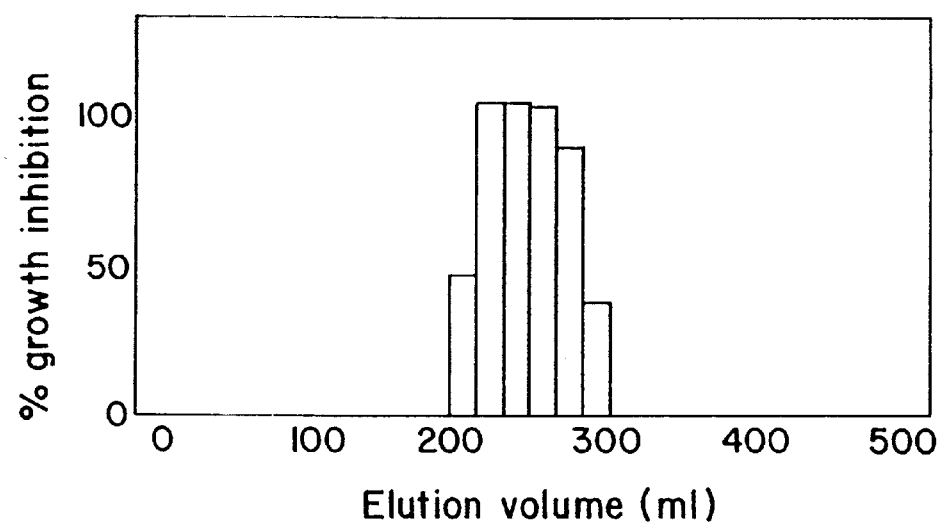
FIG. 14A shows a graph of antifungal activity of Bm-AMP1.
Figure 14B:
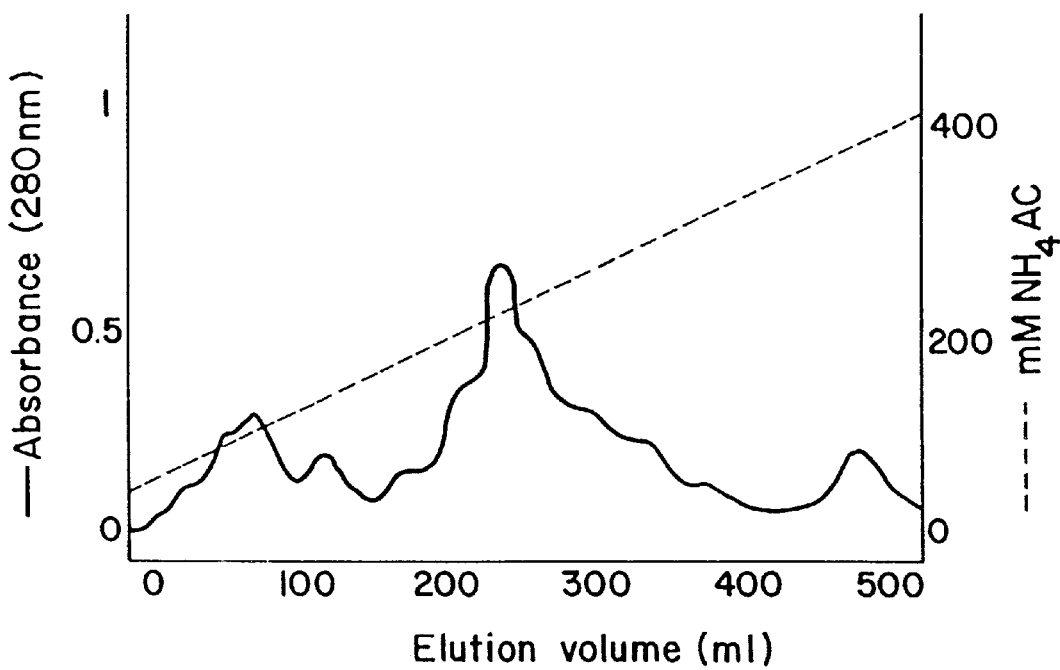
FIG. 14B shows the cation exchange chromatogram for the purification of Bm-AMP1.

Approximately 500 ml of the basic protein fraction was applied to a S-Sepharose High Performance (Pharmacia) column (10×1.6 cm) equilibrated in 50 mM $NH_4Ac$, pH 6.0. The column was eluted at 3.0 ml/min with a linear gradient of 50–750 mM $NH_4Ac$, pH 6.0 over 325 minutes. The eluate was monitored for protein by online measurement of the absorbance at 280 nm (results for Capsicum and for Briza shown in FIGS. 9B and 14B respectively) and collected in 10 ml fractions. Samples from each fraction were assayed for antifungal activity as described in Example 1 (results for Capsicum and for Briza shown in FIGS. 9A and 14A respectively).

Figure 10A:
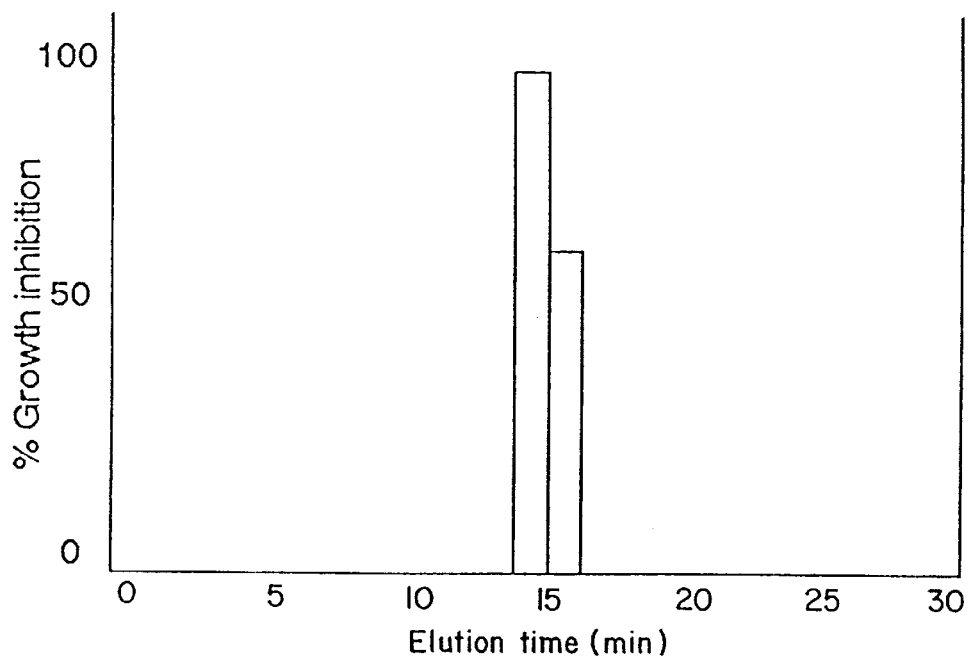
FIG. 10A shows a graph of antifungal activity Ca-AMP1.
Figure 10B:
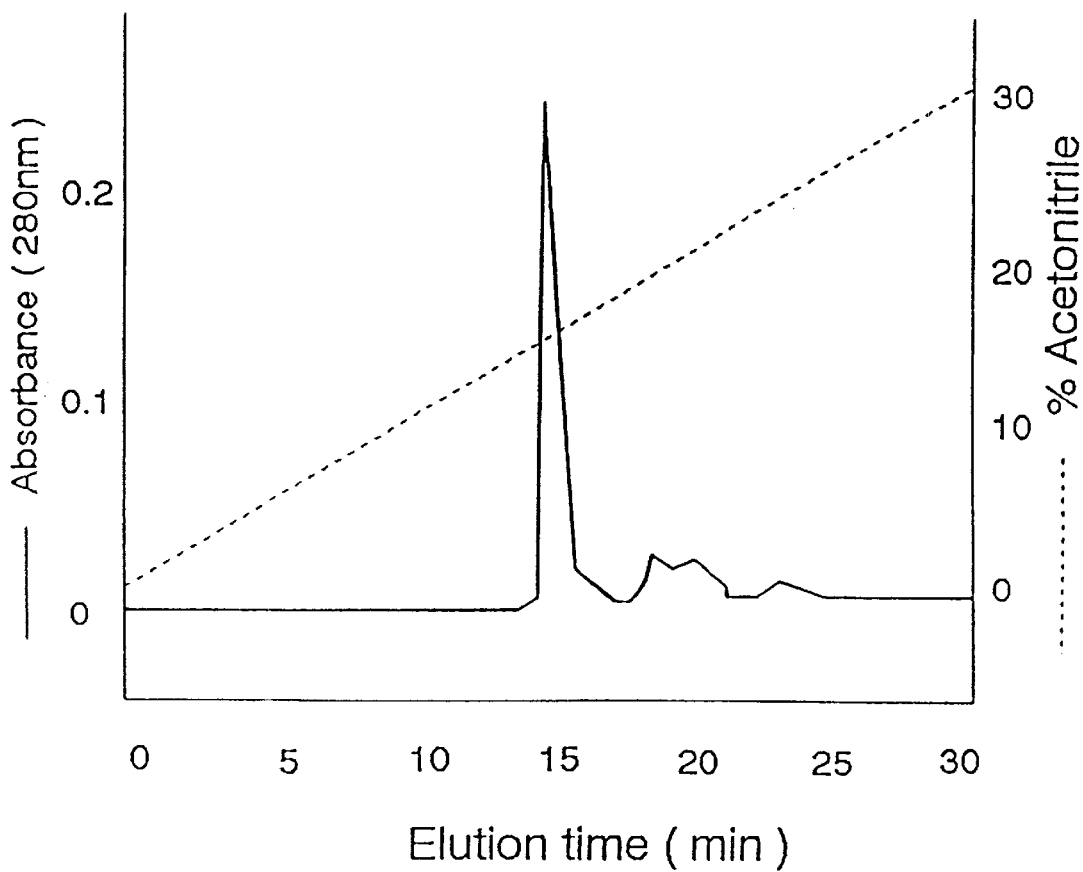
FIG. 10B shows the HPLC profile of purified Ca-AMP1.
Figure 15A:
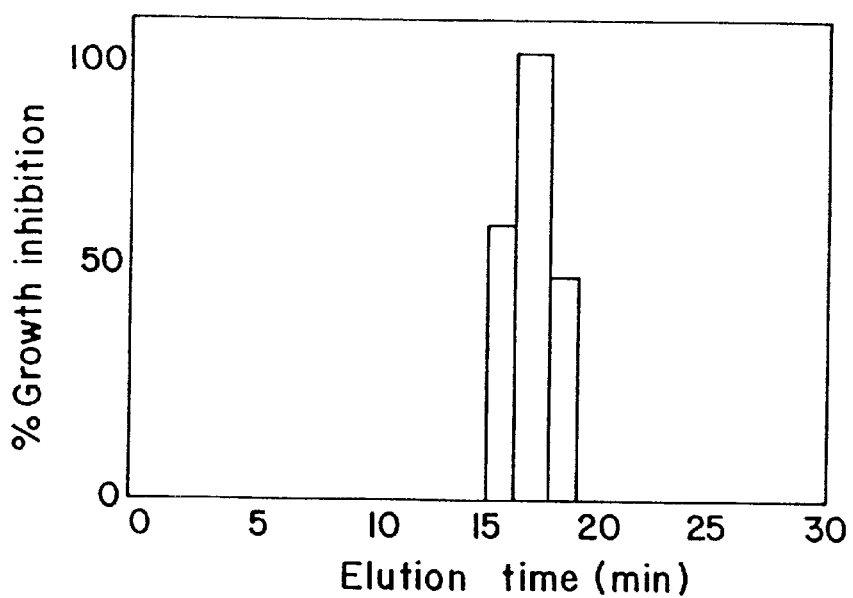
FIG. 15A shows a graph of antifungal activity of Bm-AMP1.
Figure 15B:
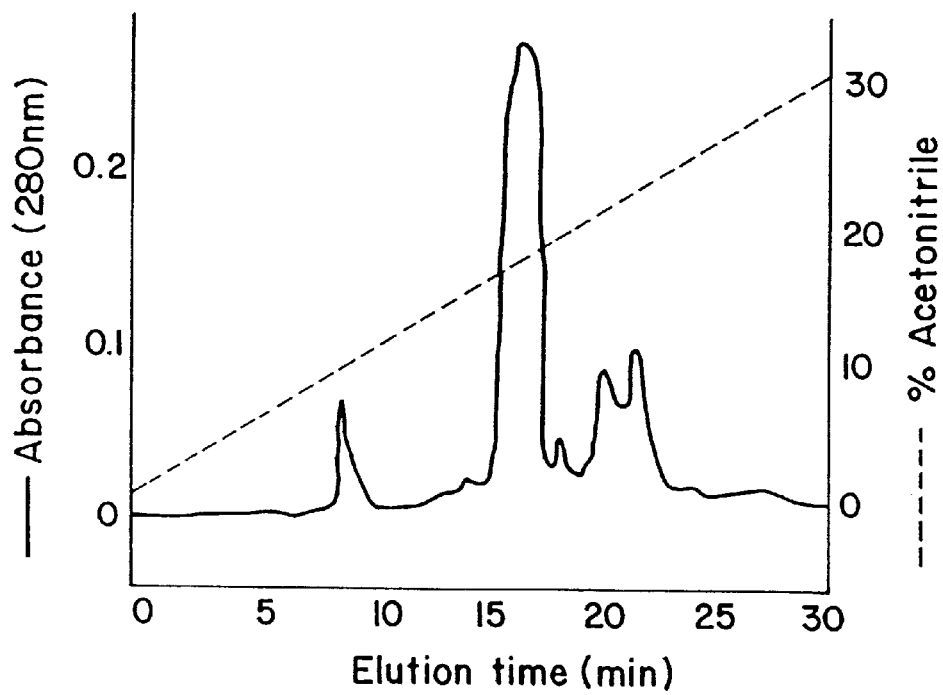
FIG. 15B shows the HPLC profile of purified Bm-AMP1.

Following chromatography, the Capsicum extract yielded a broad peak of activity eluting at around 220 mM $NH_4Ac$. The Briza extract yielded a broad peak of activity eluting at around 250 mM $HN_4Ac$. The fractions showing antifungal activity were pooled and further purified by reverse-phase HPLC. About 3 mg amounts of the peak were loaded on a PEP-S (porous silica $C_2/C_{18}$, Pharmacia) column (25×0.4 cm) equilibrated with 0.1% TFA (trifluoracetic acid). The column was developed at 1 ml/min with a linear gradient of 0.1% TFA to 100% acetonitrile/0.1% TFA over 100 minutes. The eluate was monitored for protein by online measurement of the absorption at 280 nm (results for Capsicum and for Briza shown in FIGS. 10B and 15B respectively). One ml fractions were collected, vacuum dried, and redissolved in 1 ml distilled water of which 10 μl was used in an anti-fungal assay (results for Capsicum and for Briza shown in FIGS. 10A and 15A respectively). The single well-resolved peaks of activity were called Ca-AMP1 and Bm-AMP1 respectively.

EXAMPLE 4

Molecular Structure of the Purified Antimicrobial Proteins

The molecular structure of the purified antimicrobial protein was further analysed. Sodium dodecyl sulphate polyacrylamide gel electrophoresis (SDS-PAGE) was performed on precast commercial gels (PhastGel High Density from Pharmacia) using a Phastsystem (Pharmacia) electrophoresis apparatus. The sample buffer contained 200 mM Tris-HCl (pH 8.3), 1% (w/v) SDS, 1 mM EDTA, 0.005% bromophenol blue and, unless otherwise stated, 1% (w/v) dithioerythritol (DTE). Proteins were fixed after electrophoresis in 12.5% glutaraldehyde and silver-stained according to Heukeshoven and Dernick (1985, Electrophoresis, 6:103–112). Molecular weight markers (Pharmacia) were run for comparison: 17 kDa, 14.5 kDa, 8 kDa, 6 kDa, 2.5 kDa.

4.1 Ac-AMPs

The amaranth antifungal proteins were analysed by SDS-PAGE before and after reduction with dithioerythritol. Reduced Ac-AMP1 and Ac-AMP2 both migrated as single bands with an apparent molecular weight of about 3 kDa. However, in their unreduced state, Ac-AMP1 and Ac-AMP2 yielded a 4 kDa and a 6 kDa band respectively. It appears therefore that the antifungal factors are dimeric proteins stabilized by disulphide bridges, each comprised of two identical 3 kDa subunits. Attempts to determine the molecular weight of the native Ac-AMPs by gel filtration on either Superose-12 or Superdex-75 (Pharmacia) were unsuccessful as the proteins were retarded.

FIG. 3 shows the SDS-PAGE analysis of the purified antifungal proteins: lane 1 is reduced Ac-AMP1, lane 2 is reduced Ac-AMP2, lane 3 is unreduced Ac-AMP1, lane 4 is unreduced Ac-AMP2. Two hundred nanograms of the proteins were separated on the gels.

Free cysteine thiol groups were assessed qualitatively as follows. Hundred μg amounts of reduced or unreduced proteins were dissolved in 6 M guanidinium-Cl containing 100 mM sodium phosphate buffer (pH 7) and 1 mM EDTA. The mixtures were allowed to react with 5,5'-dithionitrobenzoic acid and monitored for release of nitrothiobenzoate as described by Creighton (1989, Protein structure, a practical approach, 155–167). Reduction of the proteins was done by addition of Tris-HCl (pH 8.6) to 100 mM and dithiothreitol to 30 mM, followed by incubation at 45° C. for 1 hour. The proteins were separated from the excess reagents by reversed-phase chromatography on a $C_2/C_{18}$ silica column.

The unreduced Ac-AMPs did not contain free cysteine thiol groups, whereas the reduced proteins did, indicating that all cysteine residues participate in disulphide bonds. The presence of a relatively high number of disulphide linkages in such small polypeptides suggests that the Ac-AMPs have compact structures.

The pI values of Ac-AMP1 and Ac-AMP2 were determined by isoelectric focusing and found to be 10.3 and over 10.6 respectively. Isoelectric focusing was performed on precast Immobiline Dry Strips (Pharmacia) rehydrated in 8 M urea, using marker proteins in the pI range from 4.7 to 10.6 (Pharmacia).

4.2 Ca-AMP1

Ca-AMP1 was analysed by SDS-PAGE. After reduction with β-mercaptoethanol, Ca-AMP1 runs as a single band with an apparent molecular mass of 4 to 5 kDa. Unreduced Ca-AMP1 migrates as a single band of 14 kDa. These results show that the native Ca-AMP1 is in oligomeric protein, probably a dimer.

EXAMPLE 5

Amino Acid Sequencing of the Ac-AMPS

Cysteine residues of the antifungal proteins were modified by S-carboxyamidomethylation as follows: 100 μg amounts of purified proteins were dissolved in 150 μl 0.3 M Tris-HCl (pH 8.6) containing 30 mM DTT and reacted for 1 hour at 45° C. Iodoacetamide was added to a final concentration of 100 mM and the mixture was kept in the dark at 37° C. for 1 hour. The reaction was finally quenched by addition of DTT to a final concentration of 100 mM and allowed to react for an additional hour at 37° C. Removal of excess reagents was done by reversed-phase chromatography. The resulting protein fractions were subjected to amino acid sequence analysis in a 477A Protein Sequencer (Applied Biosystems) with on-line detection of phenylthiohydantoin amino acid derivatives in a 120A Analyser (Appl Biosystems).

Figure 4A:
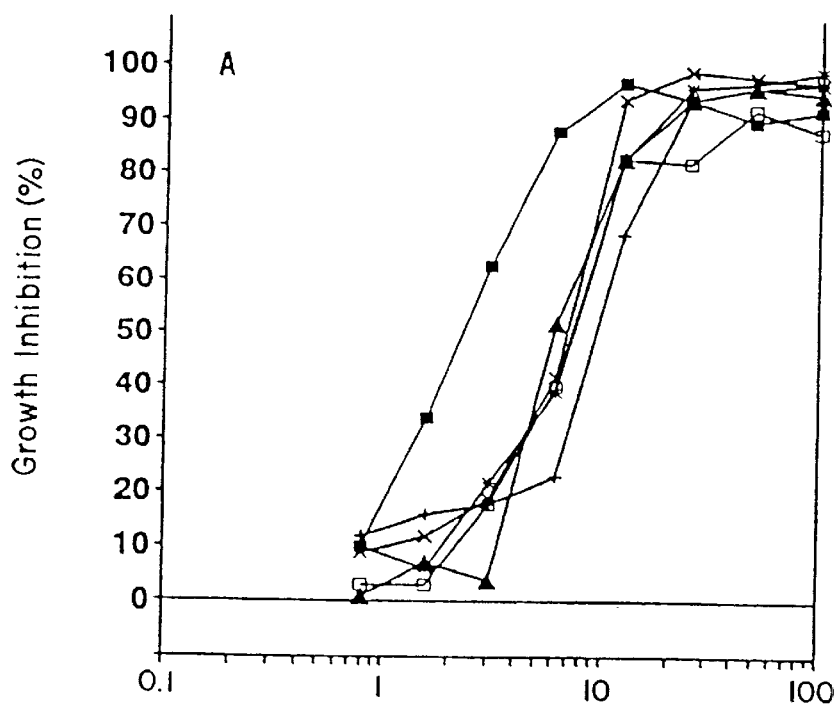
FIG. 4A shows the dose-response curves of fungal growth inhibition measured at varying concentrations of Ac-AMP1.

The amino acid sequence of the reduced and carboxyamidomethylated antifungal proteins was determined by direct N-terminal sequencing. FIG. 4A shows the N-terminal amino acid sequences of Ac-AMP1 and Ac-AMP2, shown with the sequence of Ar-AMP1. Ac-AMP1 is 29 amino acids in length, whereas Ac-AMP2 has 30 residues and Ar-AMP1 has 31 residues. The sequence of Ac-AMP2 is identical to that of Ac-AMP1 except that it has one additional amino acid at its carboxyl terminus (arginine). The Ac-AMPs are particularly rich in cysteine (6 residues), glycine (7 residues) and basic amino acids (4 and 5 residues for Ac-AMP1 and Ac-AMP2 respectively). The amino acid sequence of Ar-AMP1 is almost identical to that of Ac-AMP2: Ar-AMP1 has one additional arginine residue at the carboxyl-terminus, a conservative change at position 23 (from lysine to arginine), and two real changes at position 1 (from valine to alanine) and at position 6 (from arginine to glutamine). Like Ac-AMP2, Ar-AMP1 has 6 cysteine residues, 7 glycine residues and 5 basic residues.

Ac-AMP1 appears to be a truncated form of Ac-AMP2. It is possible that the two proteins result from the same precursor molecule by differential post-translational processing.

The theoretical isoelectric points calculated from the sequence data are 10.1 and 11.0 for Ac-AMP1 and Ac-AMP2 respectively, assuming that all cysteine residues participate in disulphide linkages. These compare well to the measured pI values given in Example 4.

FIG. 3B shows the alignment of N-terminal amino acid sequences from tobacco chitinase (Shinshi et al, 1987, Proc Natl Acad Sci USA, 84:89–93), bean chitinase (Broglie et al, 1986, Proc Natl Acad Sci USA, 83:6820–6824), hevein (Broekaert et al, 1990, Proc Natl Acad Sci USA, 87:7633–7637), wheat lectin (Raikhel and Wilkins, 1987, Proc Natl Acad Sci USA, 84:6745–6749), nettle lectin (Chapot et al, 1986, FEBS Lett, 195:231–234) and the sequence of Ac-AMP2. Sequence identities with the tobacco chitinase are indicated in capitals, conserved changes are marked in italics and non-conserved changes in lower case.

Conserved changes are considered as substitutions within the amino acid homology groups FWY, MILV, RKH, ED, NQ, ST and PAG. Gaps introduced for optimal alignment are represented by asterisks.

The amino acid sequence of the Ac-AMPs shows striking similarity to the cysteine/glycine-rich domains of Chitin-binding Plant Proteins, such as chitinases, chitin-binding lectins, and hevein. However, the Ac-AMPs also contain unique features. Sequence alignment of Ac-AMP2 and the N-terminus of a basic chitinase from tobacco (FIG. 3B) showed 14 identical amino acids and 5 conserved changes in the first 30 residues. A single gap of four amino acids had to be introduced in the N-terminal portion of Ac-AMP2 to allow optimal alignment with the Chitin-binding Plant Proteins. After introduction of this gap, all of the cysteine residues appeared at invariant positions.

EXAMPLE 6

Amino Acid Sequencing of Ca-AMP1 and Bm-AMP1

Cysteine residues were modified by S-pyridylethylation using the method of Fullmer (1984, Anal Biochem, 142, 336–341). Reagents were removed by HPLC on a Pep-S (porous silica $C_2/C_{18}$) (Pharmacia) column (25×0.4 cm). The S-pyridylethylated proteins were recovered by eluting the column with a linear gradient from 0.1% trifluoroacetic acid (TFA) to acetonitrile containing 0.1% TFA. The resulting protein fractions were subjected to amino acid sequence analysis in a 477A Protein Sequencer (Applied Biosystems) with on-line detection of phenylthiohydantoin amino acid derivatives in a 120A Analyser (Applied Biosystems).

Initial attempts to sequence Ca-AMP1 showed that the protein was N-terminally blocked. Subsequently, the S-pyridylethylated protein was unblocked with pyroglutamate amino peptidase according to the supplier's instructions (Boehringer Mannheim, FRG). The reaction was only partially successful and yielded sequence for the first 16 amino acids.

In order to obtain sequence for the C-terminus, Ca-AMP1 was digested with trypsin and three of the resulting fragments were sequenced. One was found to be blocked and represents the N-terminus. Sequencing of the other two peptides showed that they could be aligned with the sequence for the N-terminus (FIG. 11) and that the complete sequence was homologous to the cysteine/glycine-rich domain found in chitin-binding plant lectins (FIG. 12). It is possible that the sequence for Ca-AMP1 is incomplete and that there are more amino acids at the C-terminus. The finding that the peptide was N-terminally blocked and that this could be removed with amonopeptidase suggests that the N-terminal amino acid may be a glutamine.

The amino acid sequence of Bm-AMP1 is shown in FIG. 16. At two positions in the sequence there is a choice of two amino acids. At position 9 the amino acid is either arginine (R) or histidine (H), and at position 23 the amino acid is either serine (S) or asparagine (N). The purified protein fraction Bm-AMP1 may be a mixture of peptides having sequences varying at these two positions with any combination of the stated amino acids.

FIG. 12 shows the alignment of N-terminal amino acid sequences from tobacco chitinase (Shinshi et al, 1987, Proc Nat Acad Sci USA, 84:89–93), bean chitinase (Broglie et al, 1986, Proc Nat Acad Sci USA, 83:6820–6824), hevein (Broekaert et al, 1990, Pro Nat Acad Sci USA, 87:7633–7637), wheat lectin (Raikhel and Nilkins, 1987, Proc Nat Acad Sci USA, 84:6745–6749), nettle lectin (Chapot et al, 1986, FEBS Lett, 195:231–234), Ac-AMP2 (Broekaert et al, 1992, Biochemistry, 31:4308–4314; International Patent Publication Number WO92/21699) and the sequences for Ca-AMP1 and Bm-AMP1. Sequence identities and conserved changes are boxed. Conserved changes are considered as substitutions within the amino acid homology groups Phe/Trp/Tyr, Met/Ile/Leu/Val (SEQ ID NO: 20), Arg/Lys/His, Glu/Asp, Asn/Gln, Ser/Thr and Pro/Ala/Gly. Gaps introduced for maximum alignment are represented by dashes.

The amino acid sequence for Ca-AMP1 and for Bm-AMP1 shows striking similarity to the cysteine/glycine rich domain in Chitin-binding Plant Proteins. In particular, Ca-AMP1 is 65% identical to hevein. Bm-AMP1 is 35% to hevein and 45% identical to Ca-AMP1. Like the Amaranthus proteins, Ca-AMP1 and Bm-AMP1 are substantially more basic than hevein.

Both Ca-AMP1 and hevein have four basic amino acids, but Ca-AMP1 has only one acidic amino acid compared to five in hevein. If the overall basic nature of these proteins is important for their activity then substitutions of the aspartic acid at position 28 in hevein for the arginine found at this position in Ca-AMP1 would be expected to increase the specific activity of hevein. Indeed, it seems quite remarkable that Ca-AMP1 and hevein are so similar in size and amino acid sequence, but differ so dramatically in their levels and spectrum of activity.

Bm-AMP1 contains six basic amino acids and only two acidic amino acids, whereas hevein has four basic amino acids but five acidic amino acids. The overall basic profile of Bm-AMP1 may therefore be related to the increased antifungal activity of this protein compared to hevein and other Chitin-binding Plant Proteins.

FIG. 13 and FIG. 17 show one of the possible DNA sequences of the gene coding for Ca-AMP1 and Bm-AMP1 respectively. This gene sequence has been predicted from the known amino acid sequence using codons which commonly occur in dicotyledonous plants. The actual gene sequence within Capsicum or Briza many differ due to the degeneracy of the genetic code.

EXAMPLE 7

Chitin-binding Activity of the Proteins 7.1 Ac-AMPs

Because of the similarity at the amino acid sequence level between the Ac-AMPs and Chitin-binding Plant Proteins, the ability of the amaranth antifungal proteins to bind on a chitin substrate was investigated.

Micro-columns packed with chitin were loaded with either Ac-AMP1 or Ac-AMP2 and subsequently eluted at neutral pH and low pH (pH 2.8). Chitin was prepared by N-acetylation of chitosan (Sigma, St Louis, Mo.) by the method of Molano et al (1977, Anal Biochem, 83:648–656). Protein samples (50 μg) dissolved in 1 ml phosphate buffered saline (pH 7) were applied on the chitin micro-column (2.5×6 mm) and recycled three times over the column. The column was eluted five times with 1 ml phosphate buffered saline (PBS) and once with 1 ml 100 mM acetic acid (pH 2.8). Fractions (1 ml) of the eluate were desalted and concentrated by reversed-phase chromatography and finally redissolved in 50 μl sample buffer for SDS-PAGE analysis.

SDS-PAGE analysis after this affinity chromatography of Ac-AMP1 (lanes 1–4) and Ac-AMP2 (lanes 5–8). Lanes 1 and 5 included the antifungal proteins at equivalent amounts as those loaded on the columns; lanes 2 and 6 were the fractions passed through the column; lanes 3 and 7 were the fractions eluted with PBS (pH 7); lanes 4 and 8 are the fractions eluted with 100 mM acetic acid pH 2.8). It can be seen that the Ac-AMPs were absent from the fraction passed through the column and from the neutral pH washings, but instead were recovered in the low pH desorption buffer. These results indicate that both Ac-AMP1 and Ac-AMP2 exhibit affinity toward chitin.

7.2 Ca-AMP1

The similarity in sequence between Ca-AMP1 and chitin-binding plant lectins suggested that Ca-AMP1 might also bind to chitin.

Micro-chitin-columns were loaded with Ca-AMP1 and the columns washed with 50 mM $NH_4Ac$ (pH 7.0). 50 µg Ca-AMP1 was loaded onto the column (0.5×1 cm) and the eluate recycled over the column three times. The final eluate was collected. The column was washed five times with 1 ml 50 mM $NH_4Ac$ (pH 7.0) and this fraction collected. Finally, the column was washed with 1 ml 100 mM acetic acid (pH 2.8) and this acid-wash fraction collected. The collected fractions were desalted and concentrated by reverse-phase chromatography and finally dissolved in 50 µl sample buffer for SDS-PAGE analysis.

It was seen on an SDS analysis that the majority of the protein binds to the column and is eluted in the low pH desorption buffer, suggesting that Ca-AMP1 exhibits affinity to chitin.

EXAMPLE 8

Stability of the Antifungal Activity

Tests for antifungal activity were performed with 20 µl samples diluted five-fold with growth medium containing *Fusarium culmorum* spores, according to the assay method given in Example 1. untreated control samples consisted of the test proteins at 500 µg/ml in 10 mM sodium phosphat buffer (pH 7). For digestions, different proteases were added at 100 µg/ml and incubated at 37° C. for 16 hours. Heat stability tests were performed by heating aliquots of the test proteins for 10 minutes at different temperatures up to 100° C. pH stability was tested by incubation of test proteins for 1 hour in either 20 mM glycine-HCl (pH 2) or glycine-NaOH (pH 11) and subsequent dialysis for 16 hours against 10 mM sodium phosphate buffer (pH 7) using benzoylated cellulose tubing. Reduction of dishulphide bridges was done by addition of DTE at 30 mM and Tris-HCl (pH 8.6) at 300 mM. The reagents were removed by reversed-phase chromatography. For digestions, different proteases were added at 200 µg/ml and incubated at 37° C. for 3 hours. The control treatments containing only the reagents proved negative for antifungal activity after the dialysis or reversed-phase chromatography steps.

8.1 Ac-AMPs

The antifungal activity of the Ac-AMPs was resistant to digestion by proteinase K, pronase E, chymotrypsin or trypsin. Moreover, the Ac-AMPs were not affected by heat treatments at up to 100° C. for 10 minutes nor by exposure to pH conditions as extreme as pH 2 or pH 11. Reduction of their cysteine residues by dithiothreitol, however, completely abolished the antifungal activity.

The proteins are remarkably stable, since their biological activity is unaffected by protease treatments or by exposure to extreme temperatures and pH conditions. This stability may be due to a compact globular structure maintained by the relatively high number of disulphide linkages. These disulphide linkages are essential for biological activity.

8.2 Ca-AMP1 and Bm-AMP1

The antifungal activity of the purified Ca-AMP1 protein and the Bm-AMP1 protein was resistant to heat treatment at up to 80° C. for 10 minutes. Reduction of the disulphide bonds by DTE, however, completely abolished the antifungal activity. These disulphide linkages are essential for biological activity.

Treatment of Ca-AMP1 with proteinase K or pronase E reduced the antifungal activity by at least 10-fold, whereas trypsin only reduced the activity by 2-fold and chymotrypsin had no affect on activity.

EXAMPLE 9

Antifungal Potency of the Proteins 9.1 Ac-AMPs

The antifungal potency of the Ac-AMPs was assessed on fourteen different plant pathogenic fungi, using the assay described in Example 1. Growth of fungi, collection and harvest of fungal spores, and preparation of mycelial fragments were done as previously described (Broekaert et al, 1990, FEMS Microbiol Lett, 69:55–60). The following fungal strains were used: *Alternaria brassicola* MUCL 20297, *Ascochyta pisi* MUCL 30164, *Botrytis cinerea* MUCL 30158, *Cercospora beticola* strain K897, *Colletotrichum lindemuthianum* MUCL 9577, *Fusarium culmorum* IMI 180420, *Mycosphaerella fijiensis* var *fijiensis* IMI 105378, *Phytophthora infestans*, *Rhizoctonia solani* CBS 207–84, *Sclerotinia sclerotianum* MUCL 30163, *Septoria nodorum* MUCL 30111, *Trichoderma hamatum* MUCL 29736, *Verticillium dahliae* MUCL 19210, and *Venturia inaegualis* MUCL 15927.

For *C beticola, R solani, S sclerotianum, S nodorum, M fijiensis* and *P infestans*, mycelial fragments were used as inoculum. All other fungi were inoculated as spores.

Figure 4B:
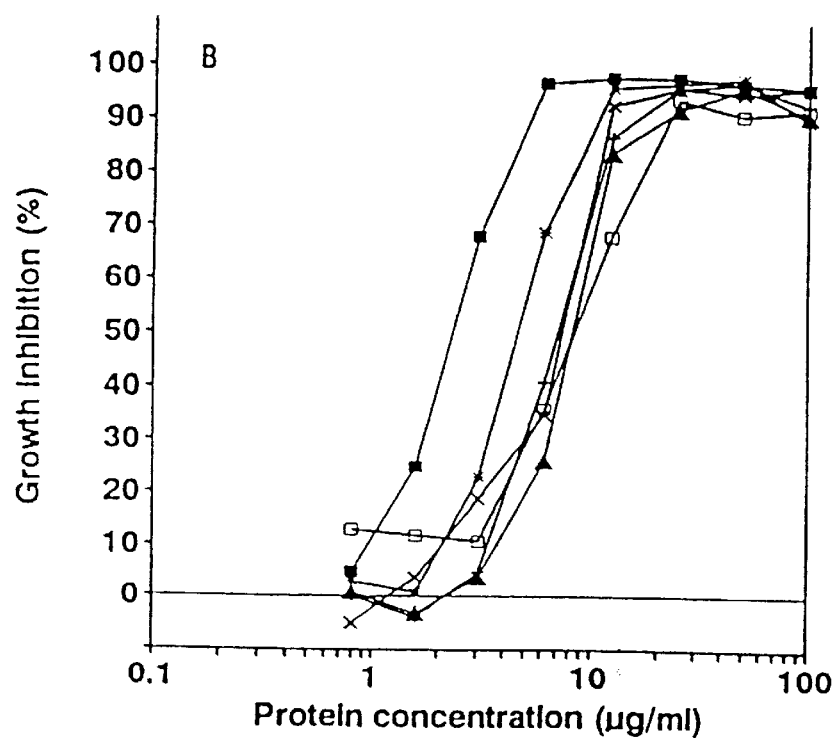
FIG. 4B shows the dose-response curves of fungal growth inhibition measured at varying concentrations of Ac-AMP2.
Figure 5A:
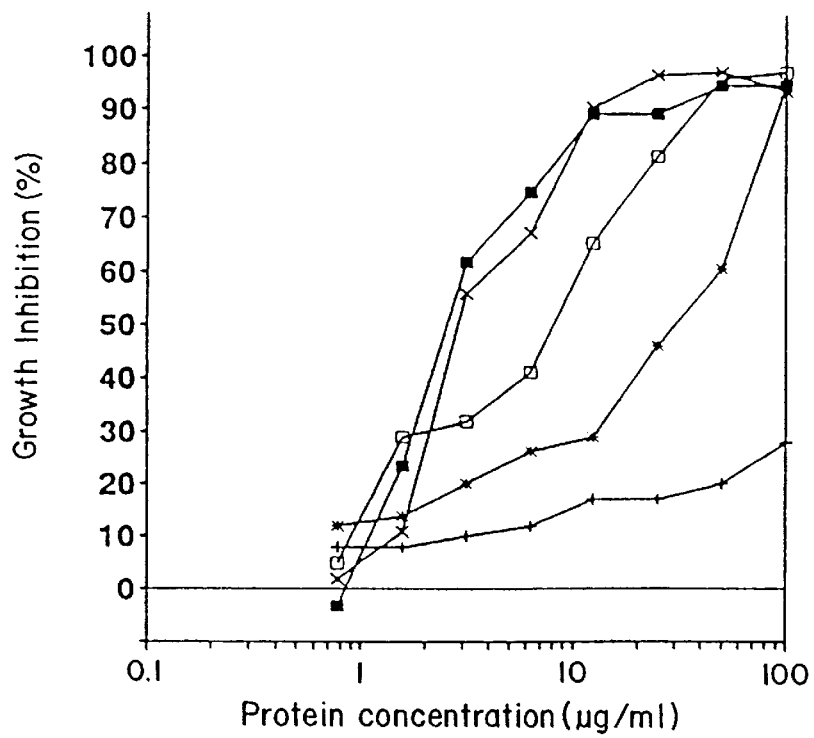
FIG. 5A shows the growth inhibition curves of *B. cinerea* measured at varying concentrations of Ac-AMP-1 with and without different additions of KCl or $CaCl_2$.
Figure 5B:
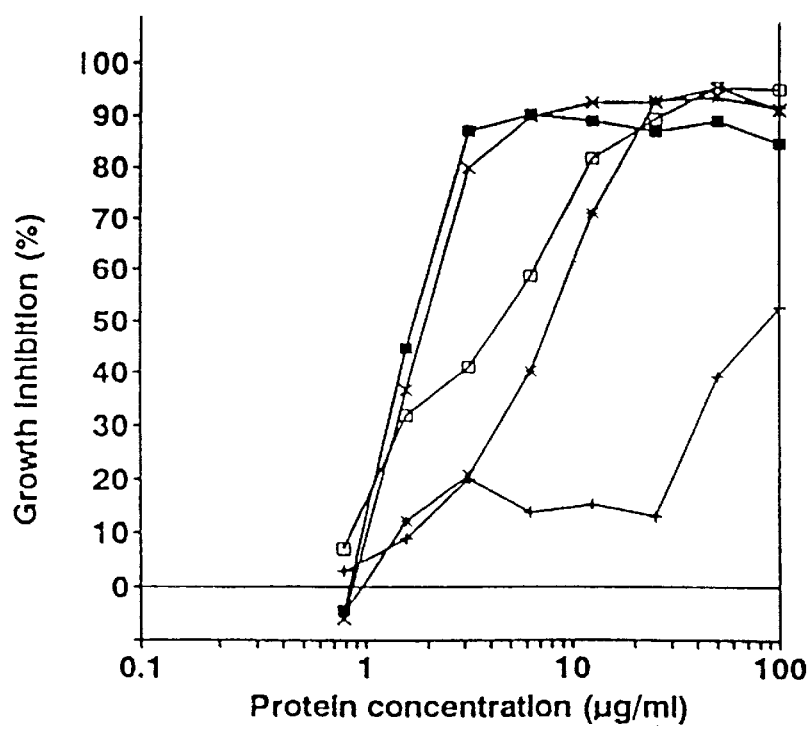
FIG. 5B shows the growth inhibition curves of *B. cinerea* measured at varying concentrations of Ac-AMP2 with and without diffent additions of KC or $CaCl_2$.

FIG. 4 shows the dose-response curves of fungal growth inhibition measured at varying concentrations of Ac-AMP1 (FIG. 4A) and Ac-AMP2 (FIG. 4B) using the following test fungi: *A brassicola* (*); *A pisi* (×); *B cinerea* (+); *C lindemuthianum* (open square); *F culmorum* (solid square); *V dahliae* (solid triangle).

The antifungal activity of the Ac-AMPs on the fourteen plant pathogenic fungi listed above was compared to that of two Chitin-binding Plant Proteins, nettle lectin and pea chitinase. Table 1 summarises the results: $IC_{50}$ is the concentration (µg/ml) required for 50% growth inhibition after 48 hours of incubation. The $IC_{50}$ values for the slow growing fungi *S nodorum* and *V inaegualis* were measured after 5 and 15 days of incubation respectively. The nettle lectin (or *Urtica dioica* agglutinin, UDA) was isolated from stinging nettle (*Urtica dioica*) rhizomes as previously described (Peumans et al, 1983, FEBS Lett, 177:99–103). Chitinase was isolated from pea pods by the method of Mauch et al (1988, Plant Physiol, 87:325–333).

TABLE 1

Antifungal activity of
Ac-AMPS, nettle lectin and pea chitinase

| | IC50 (µg/ml) | | | |
|---|---|---|---|---|
| Fungus | Ac-AMP1 | Ac-AMP2 | UDA | chitinase |
| A brassicola | 7 | 4 | 200 | 400 |
| A pisi | 8 | 8 | 1000 | >500 |
| B cinerea | 10 | 8 | >1000 | >500 |
| C beticola | 0.8 | 0.8 | ND | ND |
| C lindemuthianum | 8 | 8 | 20 | >500 |
| F culmorum | 2 | 2 | >1000 | >500 |

TABLE 1-continued

Antifungal activity of
Ac-AMPS, nettle lectin and pea chitinase

| | IC50 (μg/ml) | | | |
|---|---|---|---|---|
| Fungus | Ac-AMP1 | Ac-AMP2 | UDA | chitinase |
| M fijiensis | 3 | ND | 4 | ND |
| P infestans | 12 | ND | 4 | ND |
| R solani | 30 | 20 | 30 | ND |
| S sclerotianum | 20 | 10 | ND | ND |
| S nodorum | 20 | 20 | ND | ND |
| T hamatum | 7 | 3 | 90 | 1.5 |
| V dahliae | 6 | 5 | 80 | 500 |
| V inaequalis | ND | 3 | 1000 | ND |

ND = not determined

The concentration of Ac-AMP protein required for 50% growth inhibition after 48 hours of incubation ($IC_{50}$) varied from 0.8 to 30 μg/ml, depending on the test organism. The antifungal potency of Ac-AMP1 was almost identical to that of Ac-AMP2.

The Ac-AMPs are potent inhibitors of all fourteen fungi tested in this study. Their specificity is comparable to that of wheat thionin which also typically inhibits fungal growth with $IC_{50}$ values between 1 and 10 μg/ml (Cammue et al, 1992, J Biol Chem, 267, 2228–2233). Relative to Chitin-binding Plant Proteins, such as the nettle lectin or chitinase, the Ac-AMPs have much higher specific activities. The nettle lectin only inhibits 6 out of 11 fungi at concentrations below 100 μg/ml, whereas at this concentration the pea chitinase is only inhibitory to 1 out of 7 tested fungi.

The unique properties of the Ac-AMPs as potent inhibitors of fungal growth in vitro suggest that they may play a role in the defence of seeds or seedlings against invasion by fungal organisms.

9.2 Ca-AMP1

The antifungal potency of the purified protein was assessed on different plant pathogenic fungi, using the assay described in Example 1. Growth of fungi, collection and harvest of fungal spores, and preparation of mycelial fragments were done as previously described (Broekaert et al, 1990, FEMS Microbiol Lett, 69:55–60). The following fungal strains were used: *Alternaria brassicola* MUCL 20297, *Ascochyta pisi* MUCL 30164, *Botrytis cinerea* MUCL 30158, *Cercospora beticola* strain K897, *Colletotrichum lindemuthianum* MUCL 9577, *Fusarium culmorum* IMI 180420, *Fusarium oxysporum* f.sp. *pisi* IMI 236441, *Fusarium oxysporum* f.sp. *lycopersici* MUCL 909, *Nectria haematococca* Collection Van Etten 160-2-2, *Penicillium digitatum* (K0879), *Phoma betae* MUCL 9916, *Pyrenophora tritici-repentis* MUCL 30217, *Pyricularia oryzae* MUCL 30166, *Rhizoctonia solani* CBS 207–84, *Septoria tritici* (K1097D), *Trichoderma viride* (K1127), *Verticillium albo-atrum* (K0937), *Verticillium dahliae* MUCL 19210.

For *R solani*, mycelial fragments were used as inoculum, whereas all other fungi were inoculated as spores.

Serial dilutions of the antifungal proteins were applied to the fungi, either using growth medium A or medium B. The percent growth inhibition was measured by microspectrophotometry. The concentration required for 50% growth inhibition after 48 h of incubation ($IC_{50}$ value) was calculated from the dose-reponse curves. Results are summarised in Table 2.

TABLE 2

| | IC50 (μg/ml) | |
|---|---|---|
| Fungus | Medium A | Medium B |
| A brassicola | 20 | >500 |
| A pisi | 3 | >500 |
| B cinerea | 2 | >500 |
| C beticola | 3 | 200 |
| C lindemuthianum | 50 | >500 |
| F culmorum | 4 | >500 |
| F oxysporum pisi | >500 | >500 |
| F oxysporum lycopersici | 300 | >500 |
| N haematococca | 4 | >500 |
| P digitatum | 10 | >500 |
| P betae | 300 | >500 |
| P tritici-repentis | 70 | >500 |
| P oryzae | 5 | >500 |
| R solani | 8 | >500 |
| S tritici | 1.5 | 400 |
| T viride | 200 | >500 |
| V albo-atrum | 2 | >500 |
| V dahliae | 6 | >500 |

Assayed on a range of fungi in medium A the $IC_{50}$ values varied from 1 μg/ml to over 500 μg/ml. However, for 12 of the 18 pathogenic fungi the $IC_{50}$ value was below 50 μg/ml and for 10 of the fungi the $IC_{50}$ value was below 10 μg/ml. The results show that Ca-AMP1 is a potent and broad spectrum inhibitor of fungal growth.

The activity of Ca-AMP1 is, however, very sensitive to the ionic conditions used in the assay and it's activity is essentially abolished in high salt (medium B).

The level of antifungal activity obtained with Ca-AMP1 is comparable to that of two peptides (Ac-AMPs) previously isolated from Amaranthus seeds (Broekaert et al, 1992, Biochemistry, 31:4308–4314). Relative to Chitin-binding Plant Proteins, such as hevein or nettle lectin, Ca-AMP1 has much higher specific activity. Previously we have shown that nettle lectin inhibits only 3 of 7 fungi tested at concentrations below 100 μg/ml and none below 20 μg/ml (Broekaert et al, 1992, Biochemistry 31:4308–4314). Similarly, hevein has been reported to be much less active than even nettle lectin (Van Parijs et al, 1991, Planta 183:258–264). Despite the similarity in amino acid sequence, therefore, Ca-AMP1 can, like the Amaranthus proteins, be classed separately from the Chitin-binding Plant Proteins.

Ca-AMP1 and the Amaranthus proteins give rise to the same morphological changes in partially inhibited fungal spores. This is readily visualised when *Fusarium culmorum* spores are used in the assay and at concentrations of the proteins which are 2–4 fold below the $IC_{50}$ value. Viewed under a light microscope, the proteins cause severe branching of the emerging hyphal tips. Hevein has been reported to cause the development of thick hyphae and buds (Van Parijs et al, 1991, Planta, 183:258–264).

9.3 Bm-AMP1

The antifungal potency of the purified protein was assessed on different plant pathogenic fungi, using the assay described in Example 1. Growth of fungi, collection and harvest of fungal spores, and preparation of mycelial fragments were done as previously described (Broekaert et al, 1990, FEMS Microbiol Lett, 69:55–60). The following fungal strains were used: *Alternaria longipes* strain CBS 620.83, *Botrytis cinerea* MUCL 30158, *Cladosporium sphaerospermum* strain KO791, *Fusarium culmorum* IMI 180420, *Penicillium digitatum* strain K0879, *Septoria tritici* (K1097D), *Trichoderma viride* (K1127), *Verticillium dahliae* MUCL 19210.

All fungi were inoculated as spores. Serial dilutions of the antifungal proteins were applied to the fungi, either using growth medium A or medium B. The percent growth inhibition was measured by microspectrophotometry. The concentration required for 50% growth inhibition after 48 h of incubation ($IC_{50}$ value) was calculated from the dose-reponse curves.

The results for Bm-AMP1 are summarised in Table 3.

TABLE 3

| | IC50 (µg/ml) | |
|---|---|---|
| Fungus | Medium A | Medium B |
| A longipes | 2 | >500 |
| B cinerea | 9 | >500 |
| C sphaerospermum | 3 | >500 |
| F culmorum | 9 | >500 |
| p digitatum | 6 | >500 |
| S tritici | 1 | 400 |
| T viride | 150 | >500 |
| V dahliae | 10 | >500 |

Assayed on a range of fungi in medium A the $IC_{50}$ values varied from 1 µg/ml to 150 µg/ml. However, for six of the eight pathogenic fungi the $IC_{50}$ value was below 10 µg/ml. The results show that Bm-AMP1 is a potent and broad spectrum inhibitor of fungal growth.

The activity of Bm-AMP1 is, however, very sensitive to the ionic conditions used in the assay and it's activity is essentially abolished in high salt (medium B).

The level and spectrum of antifungal activity obtained with Bm-AMP1 is comparable to that of Ca-AMP1 and to that of the two peptides (Ac-AMPs) previously isolated from Amaranthus seeds. Relative to Chitin-binding Plant Proteins, such as hevein or nettle lectin, Bm-AMP1 has much higher specific activity. Previously we have shown that nettle lectin inhibits only 3 of 7 fungi tested at concentrations below 100 µg/ml and none below 20 µg/ml (Broekaert et al, 1992, Biochemistry 31:4308–4314). Similarly, hevein has been reported to be much less active than even nettle lectin (van Parijs et al, 1991, Planta 183:258–264). Despite the similarity in amino acid sequence, therefore, Bm-AMP1 can, like Ca-AMP1 and the Amaranthus proteins, be classed separately from Chitin-binding Plant Proteins.

EXAMPLE 10

Effect of Ions on Antifungal Activity

The specific activity of the Ac-AMPs was found to be strongly dependent on the ionic constitution of the growth medium. FIG. 7 shows the dose-response curves of Ac-AMP1 (panel A) and Ac-AMP2 (panel B) on *B cinerea* in a low ionic strength synthetic growth medium, with and without different additions of KCl or $CaCl_2$. The antagonistic effect of $K^+$ and $Ca^{2+}$ on growth inhibition of *B cinerea* caused by the Ac-AMPs is obvious. In the reference medium (solid square), containing 2.5 mM monovalent cations and 0.1 mM divalent cations, Ac-AMP1 and Ac-AMP2 had $IC_{50}$ values of 2.2 and 1.6 µg/ml respectively. Administering KCl at 10 mM (×) to this medium did not significantly affect the dose-response curves, whereas KCl at concentrations of 50 mM (open square) increased the $IC_{50}$ values by about three-fold. $CaCl_2$ had a much more dramatic antagonistic effect. When supplemented at 1 mM (*) to the reference medium, $CaCl_2$ caused a five to six-fold increase of the $IC_{50}$ values. At 5 mM $CaCl_2$ (+) the drops in specific activity were more than 50-fold. The antagonistic effect of other salts with monovalent cations, such as NaCl and $NH_4Cl$, was similar to that of KCl, whereas the effect of the salts with divalent cations, $MgCl_2$ and $BaCl_2$, was similar to that of $CaCl_2$.

These results show that the antifungal activity of the Ac-AMPs is strongly reduced by the presence of inorganic salts. The antagonistic effect of salts is primarily due to the cations; divalent cations are more potent antagonists than monovalent cations.

EXAMPLE 11

Effect of Ac-AMPs on Bacteria

Antibacterial activity was measured as described in Example 1. The following bacterial strains were used: *Bacillus megaterium* ATCC 13632, *Erwinia carotovora* strain 3912, *Escherichia coli* strain HB101 and *Sarcina lutea* ATCC 9342. The antibacterial effect of the Ac-AMPs was assessed by adding serial dilutions of the proteins to bacterial suspensions. The highest test concentration was 500 µg/ml (final concentration). Results are shown in Table 4.

TABLE 4

| Antibacterial activity of the Ac-AMPS | | |
|---|---|---|
| | IC50 (µg/ml) | |
| Bacteria | Ac-AMP1 | Ac-AMP2 |
| B megaterium | 40 | 10 |
| S lutea | 250 | 40 |
| E carotovora | no inhibition | |
| E coli | no inhibition | |

The Ac-AMPs inhibited growth of the Gram-positive bacteria, *B megaterium* and *S lutea*. However, the Ac-AMPs (at 500 µg/ml) did not inhibit growth of the gram-negative bacteria E carotovora and *E coli*.

EXAMPLE 12

Anti-bacterial and Anti-yeast Activity of Ca-AMP1 and of Ba-AMP1

The purified proteins were assessed for effect on the growth of the following bacteria: *Bacillus megaterium* ATCC 13632, *Escherichia coli* strain HB101 and *Pseudomonas aeurogenasa* NCIB 8295; and for its effect on the growth of *Saccharomyces cerevisiae* JRY188. Bioassays were carried out as described in Example 1. The results are summarised in Table 5. Ca-AMP1 and Bm-AMP1 each strongly inhibited the growth of *B megaterium* and *S cerevisiae* but had little or no effect on the two Gram negative bacteria tested.

TABLE 5

| Activity of Ca-AMP1 and Bm-AMP1 on bacteria and yeast | | |
|---|---|---|
| | IC50 (µg/ml) | |
| | Ca-AMP1 | Bm-AMP1 |
| B megaterium | 20 | 10 |
| P aeurogenasa | 500 | 500 |
| E coli | >800 | >800 |
| S cerevisiae | 30 | 15 |

EXAMPLE 13

Effect of the Ac-AMPs on Cultured Human Cells

The Ac-AMPs were evaluated for their potential toxic effects on mammalian cells.

Human cell toxicity assays were performed either on umbilical vein endothelial cells (Alessi et al, 1988, Eur J Biochem, 175, 531–540) or skin-muscle fibroblasts (Van Damme et al, 1987, Eur J Immunol, 17, 1–7) cultured in 96-well microplates. The growth medium was replaced by 80 µl of serum-free medium (Optimem 1 for endothelial cells or Eagle's minimal essential medium (EMEM) for fibroblasts, both from GIBCO), to which 20 µl of a filter-sterilized test solution was added. The cells were further incubated for 24 hours at 37° C. under a 5% $CO_2$ atmosphere with 100% relative humidity. The viability of the cells was assessed microscopically after staining with trypane blue (400 mg/l in phosphate buffered saline, PBS) for 10 minutes. Alternatively, cells were stained with neutral red (56 mg/l in PBS) for 2 h at 37° C. Cells were lysed in acidic ethanol (100 mM sodium citrate, pH 4, containing 50% ethanol) and scored for release of the dye by microspectrophotometry at 540 nm.

When added at up to 500 µg/ml to either cultured human umbilical vein endothelial cells or human skin-muscle fibroblasts, neither Ac-AMP1 nor Ac-AMP2 affected cell viability after 24 h of incubation. In contrast, β-purothionin administered at 50 µg/ml decreased the viability of both cell types by more than 90%.

EXAMPLE 14

Molecular Cloning of Ac-AMP2 cDNA

Fully matured seeds of *Amaranthus caudatus* were collected from outdoor grown plants, immediately frozen in liquid nitrogen and stored at −80° C. Total RNA was extracted from 5 g of pulverized seeds by the method of De Vries et al (1988, Plant Molecular Biology Manual, B6, 1–13) using 6 ml of a 1:2 phenol:RNA extraction buffer mixture and 2 ml of chloroform per g tissue. Poly $(A)^+$ RNA was purified by oligo (dT)-cellulose affinity chromatography as described by Silflow et al (1979, Biochemistry, 18, 2725–2731) yielding about 7 µg of poly $(A)^+$ RNA. Double-stranded cDNAs were prepared from 1.5 µg of poly $(A)^+$ RNA according to Gubler and Hoffman (1983, Gene, 25, 263–269) and ligated to EcoRI/NotI adaptors using the cDNA Synthesis Kit of Pharmacia. The cDNAs were cloned into the λ ZAP II phage vector (Stratagene) and packaged in vitro with the Gigapack II Gold packaging system (Stratagene) according to the manufacturer's instructions.

A DNA probe for screening of the cDNA library was produced by polymerase chain reaction (PCR) as follows. Two degenerate oligonucleotides were synthesized: OWB13 (5'GTNGGNGARTGKGTNMGNGG) (SEQ ID NO: 1) and OWB14 (5'CCRCARTAYTTNGGNCCYTTNCC) (SEQ ID NO: 2). OWB13 corresponds to amino acids 1 to 7 of Ac-AMP1 and has a sense orientation. OWB14 corresponds to amino acids 22 to 29 of Ac-AMP1 and has an antisense orientation. PCR was performed with the Taq polymerase under standard conditions (Sambrook et al, 1989, Molecular Cloning, Cold Spring Harbour Lab Press) using OWB13 and OWB14 as amplimers and 25 ng of cDNA as target DNA. The temperature programme included an initial step at 94° C. for 5 min, 30 cycles (94° C. for 1 min; 45° C. for 2 min; 72° C. for 3 min) and a final step at 72° C. for 10 min. The 100 bp PCR amplification product was purified on a 3% agarose (NuSieve, FMC) gel and reamplified by PCR under the same conditions except that the reaction mixtures contained 130 µM dTTP and 70 µM digoxigenin-11-dUTP instead of 200 µM dTTP. The digoxigenin-labelled PCR product was purified on a 3% NuSieve agarose gel.

About 100,000 plaque forming units of the λ ZAP II cDNA library were screened with the digoxigenin-labelled PCR product by in situ plaque hybridization using nylon membranes (Hybond-N, Amersham). Membranes were air-dried and DNA was crosslinked on the membranes under UV light (0.15 $J/cm^2$). Hybridization was performed for 16 hours at 65° C. in 5×SSC, 1% blocking reagent (Boehringer Mannheim), 0.1% N-lauroylsarcosine, 0.02% sodium dodecylsulphate containing 10 ng/ml of heat denatured digoxigenin-labelled probe. Non-specifically bound probe was removed by rinsing twice for 5 min in 2×SSC/0.1% SDS at 25° C. and twice for 15 min in 0.1×SSC/0.1% SDS at 60° C. Detection of the probe was done using anti-digoxigenin antibodies linked to alkaline phosphatase (Boehringer Mannheim) and its substrate 5-bromo-4-chloro-3-indolyl phosphate (Boehringer Mannheim) according to the manufacturer's instructions. Positive plaques were purified by two additional screening rounds with the same probe under the same conditions. Inserts from purified plaques were excised in vivo into the pBluescript phagemid form with the aid of the helper phage R408, according to the instructions of Stratagene. Nucleotide sequencing was done with an ALF automated sequencer (Pharmacia) using fluoresceine-labelled M13 forward and reverse primers (Pharmacia). Sequence analysis was performed by the Intelligenetics PC-gene software.

Inserts from ten different positive clones were released by EcoRI digestion and their sizes compared by agarose electrophoresis. The clone with the longest insert (AC1) was subjected to nucleotide sequence analysis. AC1 is 590 nucleotides long and contains an open reading frame of 86 amino acids. The 25 amino-terminal amino acids have a predictable signal peptide structure obeying the (-1,-3)-rule (Von Heijne, 1985, Mol Biol, 184, 99–105). The deduced amino acid sequence of the region following the putative signal peptide is identical to the 30-amino acid sequence of mature Ac-AMP2 as determined by protein sequencing. In addition, the mature protein domain is extended by a 31-amino acids carboxy-terminal domain. This carboxy-terminal extension may play a role in the subcellular targeting of Ac-AMP2. AC1 has 45-nucleotide and 284-nucleotide untranslated regions at the 5' and 3' end, respectively. The 3' end untranslated region is not terminated by a poly(A) tail, indicating that AC1 is not a full length cDNA clone.

All of the other nine sequenced positive clones had deduced amino acid sequences identical to that of AC1. They differed from each other by various degrees of truncation at the 5' or 3' end. The fact that the 10 sequenced clones all contained an arginine at position 30 of the mature protein domain suggests that Ac-AMP1 and Ac-AMP2 are both derived from the same precursor preprotein.

The carboxy-terminal extension peptide did not show relevant homology either at the amino acid or nucleotide level with any of the entries from the Swiss-Prot (release 20) or EMBL gene bank (release 29), respectively. The structure of the Ac-AMP2 cDNA thus appears to be unique and obviously different from that of known genes encoding Chitin-binding Plant Proteins.

FIG. 6 shows the nucleotide sequence and deduced amino acid sequence of clone AC1. The putative signal sequence is underlined and the sequence of mature Ac-AMP 2 is boxed. The stop codon is marked with an asterisk.

EXAMPLE 15

Molecular Cloning of Ca-AMP1 and Bm-AMP1 cDNAs

From outdoor grown plants, seeds at 6 different developmental stages are collected, frozen in liquid nitrogen and stored at −80° C. After pulverization, total RNA is extracted from 15 g of a mixture of the 6 different developmental stages, using the method of De Vries et al (1988, Plant Molecular Biology Manual, B6, 1–13) with the exception that 6 ml of a 1:2 phenol:RNA extraction buffer mixture and 2 ml of chloroform are used per g of tissue. Poly (A)$^+$ mRNA is purified by affinity chromatography on oligo(dT)-cellulose as described by Siflow et al (1979, Biochemistry 18, 2725–2731). Double stranded cDNAs are prepared from 1.5 $\mu$g of poly(A)$^+$ RNA according to Gubler and Hoffman (1983, Gene 25, 263–269) and ligated to EcoRI/NotI adaptors using the cDNA Synthesis Kit of Pharmacia.

The cDNAs are cloned into the lambda ZAPII phage vector (Stratagene) according to the manufacturers instructions. A DNA probe for screening the cDNA library is produced by polymerase chain reaction (PCR) as follows. Two degenerate oligonucleotides are synthesized, corresponding to a run of amino acids of Ca-AMP1 or Bm-AMP1: one has a sense orientation and the other has an antisense orientation. Both primers have the AAAGAATTC (i.e. AAA followed by the EcoRI recognition sequence) sequence at their 5' ends. PCR is performed with the Tag polymerase under standard conditions (Sambrook et al, 1989, Molecular Cloning, Cold Spring Harbor Laboratory Press) using the oligonucleotides as amplimers and 25 ng of cDNA as target DNA. The temperature programme includes an initial step at 94° C. for 5 min, 30 cycles (94° C. for 1 min; 45° C. for 2 min, 72° C. for 3 min) and a final step at 72° C. for 10 min. The PCR amplification product is purified on a 3% agarose (NuSieve, FMC) gel. This PCR product is partially reamplified using degenerate oligonucleotides. This PCR amplification product is again purified on a 3% agarose (NuSieve, FMC) gel and reamplified by PCR under the same conditions except that the reaction mixture contained 130 $\mu$M dTTP and 70 $\mu$M digoxigenin-11-dUTP instead of 200 $\mu$M dTTP. The digoxigenin-labeled PCR product is purified on a 3% NuSieve agarose gel. About 10,000 plaque forming units of the lambda ZAPII cDNA library are screened with the digoxigenin-labeled PCR product by in situ plaque hybridization using nylon membranes (Hybond-N, Amersham). Membranes are air-dried and DNA is crosslinked to the membranes under UV light (0.15 J/cm$^2$). Hybridization is performed for 16 h at 64° C. in 5×SSC, 1% blocking reagent (Boehringer Mannheim), 0.1% N-lauroylsarcosine, 0.02% sodium dodecylsulphate containing 10 ng/ml of heat denatured digoxigenin-labeled probe. Non-specifically bound probe is removed by rinsing two times 5 min in 2×SSC/0.1% SDS at 25° C. and two times 15 min in 0.1×SSC/0.1% SDS at 60° C. Detection of the probe is done using anti-digoxigenin antibodies linked to alkaline phosphatase (Boehringer Mannheim) and its substrate 5-bromo-4-chloro-3-indolyl phosphate (Boehringer Mannheim) according to the manufacturers instructions. Positive plaques are purified by two additional screening rounds with the same probe under the same conditions. Inserts from purified plaques are excised in vivo into the pBluescript phagemid form with the aid of the helper phage R408. The inserts from different positive clones are excised by EcoRI digestion and their sizes compared by agarose gel electrophoresis. Some of the clones are subjected to nucleotide sequence analysis. The clones with the largest insert may have an open reading frame corresponding to Ca-AMP1 or Bm-AMP1, as could be determined by comparison to the experimental N-terminal amino acid sequences. The full-length cDNA clones may differ from each other in the length of their 5' and 3' end untranslated regions and polyadenylation signals.

In order to obtain a full-length cDNA, another approach may be followed. PCR is performed under standard conditions using an antisense oligonucleotide in combination with the M13 universal primer at one hand and the M13 reverse primer at the other hand. The last nucleotides of the oligonucleotide form the inverted complementary sequence of part of the 3' untranslated region immediately flanking the poly-A tail of the less-than-full-length cDNA clone. This sequence is extended to the 5' end with the GAATTC EcoRI recognition site preceded by the nucleotides 'ATA'. As a template, either 2 $\mu$g of total cDNA or 10$^5$ recombinant phages are used. In both cases, 3 separate reactions are set up. Prior to amplification, phages are lysed by an initial step in the PCR temperature programme of 5 min at 99° C. to liberate the phage DNA. The size of the amplification products is determined by electrophoresis on a 3% agarose (NuSieve, FMC) gel. Products are obtained with sizes corresponding to inserts of different length, including a full-length cDNA clones if one is present in the cDNA library.

EXAMPLE 16

Construction of the Expression Vectors pAC11 and pAC12 (Encoding Ac-AMP2)

Two different expression cassettes were constructed based on two portions of the insert of clone AC1.

Figure 7A:
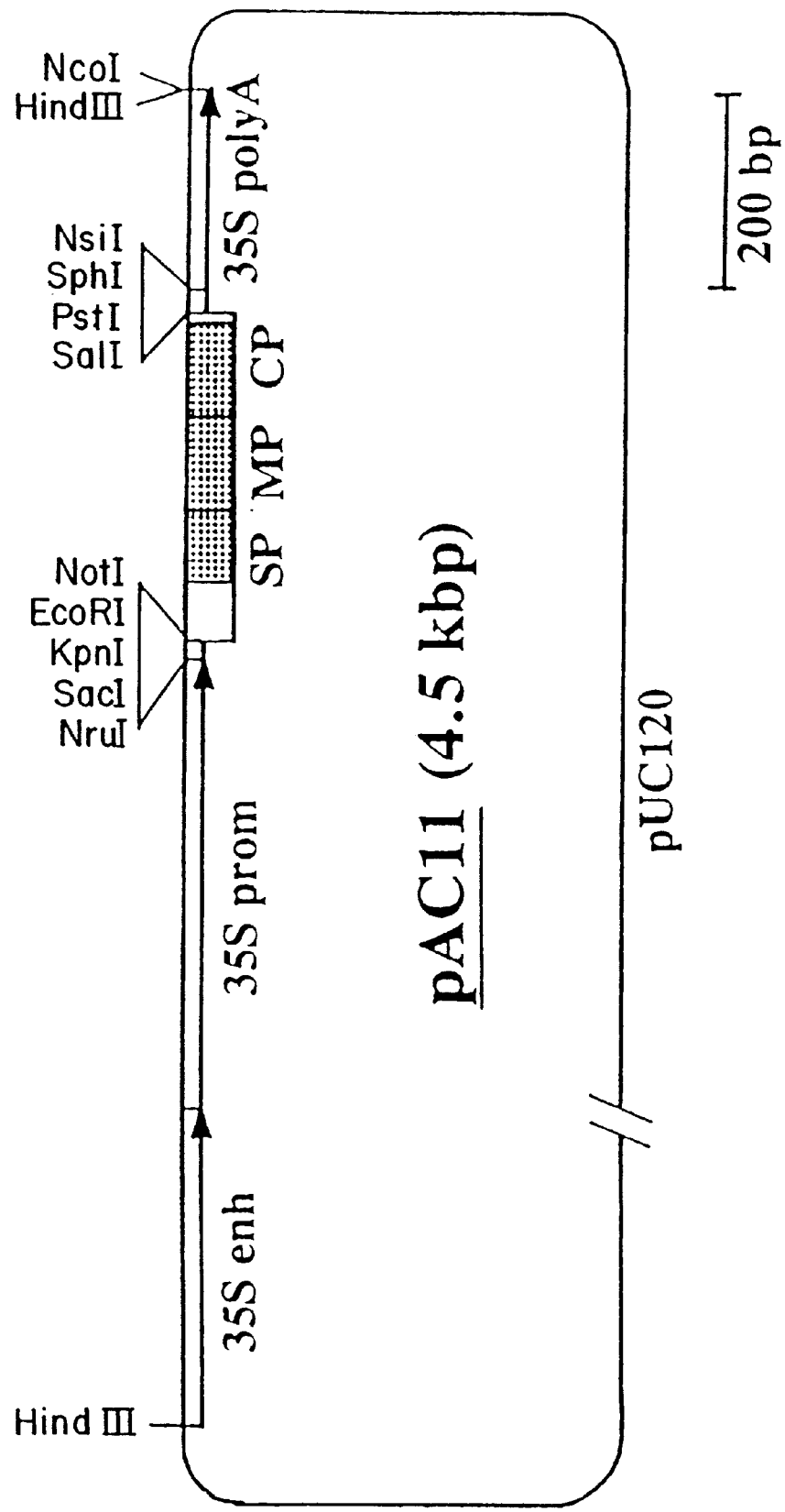
FIGS. 7A and 7B shows the structure of the expression vectors pAC11 and pAC12.
Figure 7B:
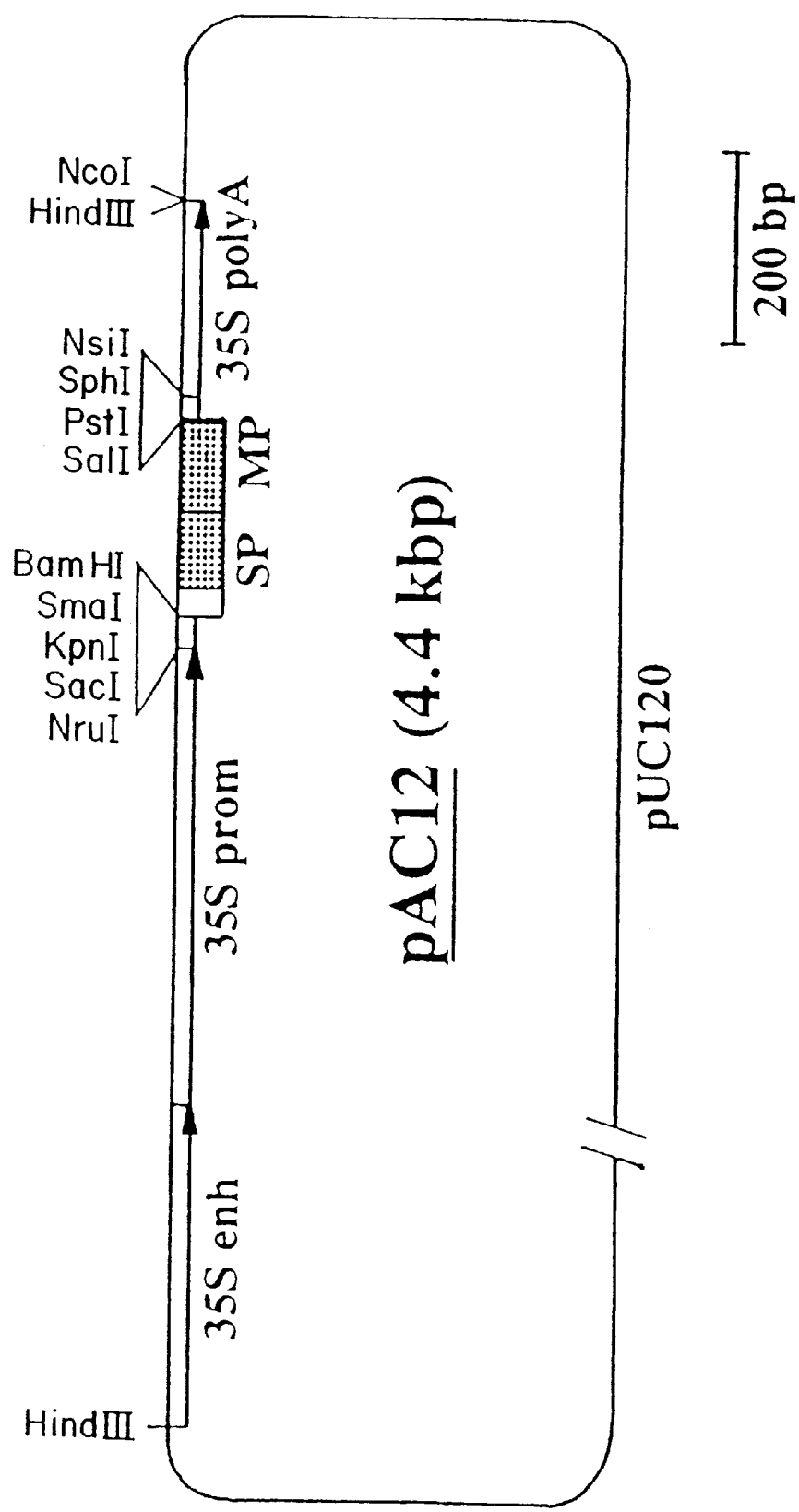

The first expression vector (pAC11, as shown in FIG. 7A) contains the full coding region of Ac-AMP2 cDNA flanked at its 5' end by the strong constitutive promoter of the 35S RNA of cauliflower mosaic virus, CaMV35S (Odell et al, 1985, Nature, 313, 810–812) with a duplicated enhancer element to allow for high transcriptional activity (Kay et al, 1987, Science, 236, 1299–1302). The Ac-AMP2 cDNA coding region includes the signal peptide (SP), the mature protein (MP), and the carboxy-terminal extension peptide (CP) as shown in FIG. 7A. The coding region of Ac-AMP2 cDNA is flanked at its 3'side by the CaMV25S polyadenylation sequence. The plasmid backbone of this vector is the phagemid pUC120 ( Vieira and Messing, 1987, Methods Enzymol, 153, 3–11).

pAC11 was constructed from clone AC1 as follows. Clone AC1 consists of the Ac-AMP2 cDNA (shown in FIG. 6) cloned into the EcoRI site of pBluescript SK(+) (from Stratagene) such that the 5'end faces the M13 universal primer binding site. AC1 was digested with EcoRV (cuts within the SK polynker of pBluescript) and NheI (cuts internally in the Ac-AMP2 cDNA sequence at base position 315 which is 9 bases downtream of stop codon). The EcoRV/HheI 332 bp fragment was subcloned into the expression vector pFAJ3002 which was pre-digested with SmaI and XbaI. PFAJ3002 is derivative of the expression vector pFF19 (Timmermans et al, 1990 Biotechnology, 14, 333–344) in which the unique EcoRI site is replaced by a HindIII site.

The second expression vector (pAC12, shown in FIG. 7B) contains an open reading frame coding for the signal peptide (SP) and mature domain (MP) of the Ac-AMP preprotein. This open reading frame is flanked at its 5'side by the duplicated CaMV35S promoter and at its 3'side by the CaMV35S polyadenlyation sequence.

pAC12 was constructed as follows. A 216 bp fragment was amplified by polymerase chain reaction using AC1 as DNA template and OWB32, OWB33 as sence and antisense primers respectively. The primer OWB32 (5' AATTGGATCCAGTCAAGAGTATTAATTAGG) (SEQ ID NO: 3) corresponds to nucleotides 17 to 36 of Ac-AMP2 cDNA and introduces a BamHI site at the 5' end of the PCR amplification product. The primer OWB33 (5' AATTGRCGACTCAACGGCCACAGTACTTTGGGCC) (SEQ ID NO: 4) corresponds to nucleotides 190 to 210 of Ac-AMP2 cDNA and links an inframe stop codon and a SalI site to the 3' end of the PCR products. Both OWB32 and OWB33 have a 4 bp random sequence at the 5' end prior to the restriction site. The PCR product was digested with BamHI and SalI and subsequently subcloned into the expression vector pFAJ3002, previously digested with the same restriction enzymes.

EXAMPLE 17

Construction of the Plant Transformation Vectors pAC111 and pAC112 (Encoding Ac-AMP2)

The expression vector pAC11 and pAC12 were digested with HindIII and the fragments containing the Ac-AMP2 cDNA expression cassettes were subcloned into the unique HindIII site of pBin19Ri. pBin19Ri is a modified version of the plant transformation vector pBin19 (Bevan, 1984, Nucleic Acids Research, 12:22, 8711–8721) wherein the unique EcoR1 and HindIII sites are switched and the defective npt II expression cassette (Yenofsky et al, 1990, Proc Natl Acad Sci USA, 87:3435–3439) is replaced by the npt II expression cassette described by An et al (1985, EMBO J, 4:277–284).

Figure 8:
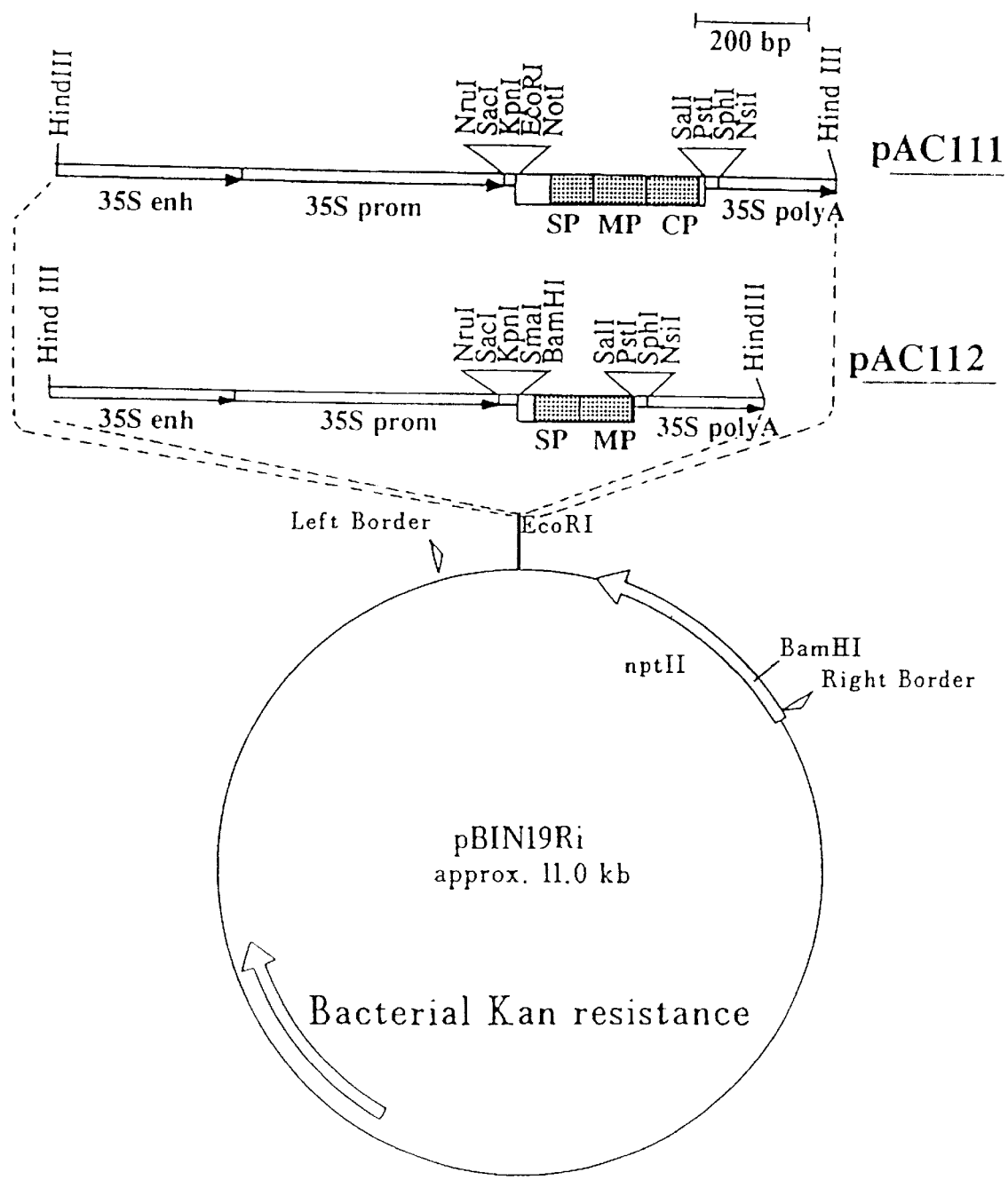
FIG. 8 shows the structure of the plant transformation vectors pAC111 and pAC112.

The plant transformation vector containing the pAC11 expression cassette was designated pAC111, while the transformation vector containing the pAC12 expression cassette was designated pAC112. The structure of the two transformation vectors is shown in FIG. 8. pAC111 includes DNA encoding the AC-AMP2 signal peptide (SP), mature protein (MP), and carboxy-terminal extension peptide (CP); pAC112 includes DNA encoding the Ac-AMP2 signal peptide (SP) and mature protein (MP).

EXAMPLE 18

Plant Transformation

The disarmed *Agrobacterium tumefaciens* strain LBA4404 [pAL4404] (Hoekema et al, 1983, Nature, 303:179–180) may be transformed by either of the vectors pAC111 or pAC112, using the method of de Framond A et al (Biotechnology, 1:262–9).

Tobacco transformation may be carried out using leaf discs of *Nicotiana tabacum* Samsun based on the method of Hozsch RB et al (1985, Science, 227, 1229–31) and co-culturing with Agrobacterium strains containing pAC111 or pAC112. Co-cultivation may be carried out under selection pressure of 100 µg/ml kanamycin. Transgenic plants (transformed with pAC111 or pAC112) may be regenerated on media containing 100 µg/ml kanamycin. These transgenic plants may be analysed for expression of the newly introduced genes using standard Western blotting techniques. Transgenic plants may also be analysed for increased resistance to fungal or bacterial diseases.

Plants capable of constitutive expression of the introduced genes may be selected and self-pollinated to give seed. The progeny of the seed exhibiting stable integration of the Ac-AMP genes would be expected to show typical Mendelian inheritance patterns for the Ac-AMP genes.

EXAMPLE 19

Construction of an Expression Vector Encoding Ca-AMP1 or Bm-AMP1

An expression vector is constructed, containing the full coding region of the Ca-AMP1 or Bm-AMP1 DNA flanked at its 5' end by the strong constitutive promoter of the 35S RNA of the cauliflower mosaic virus (Odell et al, 1985, Nature 313, 810–812) with a duplicated enhancer element to allow for high transcriptional activity (Kay et al, 1987, Science 236, 1299–1302). The coding region of the Ca-AMP1/Bm-AMP1 DNA is flanked at its 3' end side by the polyadenylation sequence of 35S RNA of the cauliflower mosaic virus (CaMV35S). The plasmid backbone of this vector is the phagemid pUC120 (Vieira and Messing 1987, Methods Enzymol. 153, 3–11). The expression vector is constructed as follows. A cDNA clone consisting of the Ca-AMP1/Bm-AMP1 DNA is cloned into the BamHI/SalI sites of pEMBL18+, Boehringer). The BamHI/SalI fragment is subcloned into the expression vector pFAJ3002 which was pre-digested with BamHI and SalI. pFAJ3002 is a derivative of the expression vector pFF19 (Timmermans et al, 1990, J. Biotechnol. 14, 333–344) of which the unique EcoRI site is replaced by a HindIII site.

EXAMPLE 20

Construction of a Plant Transformation Vector Encoding Ca-AMP1 or Bm-AMP1

The expression vector from Example 19 is digested with HindIII and the fragment containing the Ca-AMP1/Bm-AMP1 DNA expression cassette is subcloned into the unique HindIII site of pBin19Ri. pBin19Ri is a modified version of the plant transformation vector pBin19 (Bevan 1984, Nucleic Acids Research 12, 8711–8721) wherein the unique EcoRI and HindIII sites are switched and the defective nptII expression cassette (Yenofsky et al. 1990, Proc. Natl. Acad. Sci. USA 87: 3435–3439) is introduced.

EXAMPLE 21

Plant Transformation

The disarmed *Agrobacterium tumefaciens* strain LBA4404 (pAL4404)(Hoekema et al, 1983, Nature 303, 179–180) is transformed with the vector made in Example 20 using the method of de Framond et al (BioTechnology 1, 262–269).

Tobacco transformation is carried out using leaf discs of *Nicotiana tabacum* Samsun based on the method of Hotsch et al (1985, Science 227, 1229–1231) and co-culturing with Agrobacterium strains containing pFRG8. Co-cultivation is carried out under selection pressure of 100 µg/ml kanamycin. Transgenic plants (transformed with pFRG8) are regenerated on media containing 100 µg/ml kanamycin. These transgenic plants may be analysed for expression of the newly introduced genes using standard western blotting techniques. Plants capable of constitutive expression of the introduced genes may be selected and self-pollinated to give seed. F1 seedlings of the transgenic plants may be further analysed.

We claim:

1. An isolated protein comprising-cysteine-cysteine-(serine or threonine)-(one amino acid)-(tryptophan, tyrosine or phenylalanine)-glycine-(tryptophan, tyrosine or phenylalanine)-cysteine-glycine-(SEQ ID NO:21), wherein said protein has a ratio of basic amino acids to acidic amino acids of 5:1, 4:1 or 3:1, and wherein said protein also has antimicrobial and/or antifungal activity, said antifungal activity being at least one order of magnitude greater than the antifungal activity of hevein or nettle lectin.

2. The protein of claim 1 wherein said antimicrobial and/or antifungal activity is activity against plant pathogenic fungi resulting in hyphal branching.

3. A composition containing the protein of claim 1 and at least one other component.

4. A composition containing the protein of claim 2 and at least one other component.

5. A process of combatting fungi or bacteria which comprises exposure to a protein as claimed in claim 1.

6. A process of combatting fungi or bacteria which comprises exposure to a protein as claimed in claim 2.

7. An isolated protein of claim 1 wherein said protein comprises a central cysteine motif of cysteine-(four amino acids)-cysteine-cysteine-(five amino acids)-cysteine-(six amino acids)-cysteine (SEQ ID NO:22).

8. The protein claim 7, wherein said antimicrobial and/or antifungal activity is activity against plant pathogenic fungi resulting in hyphal branching.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

GTNGGNGART GKGTNMGNGG                                                    20

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

CCRCARTAYT TNGGNCCYTT NCC                                                23

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

AATTGGATCC AGTCAAGAGT ATTAATTAGG                                         30

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

AATTGTCGAC TCAACGGCCA CAGTACTTTG GGCC                                    34

(2) INFORMATION FOR SEQ ID NO:5:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Val Gly Glu Cys Val Arg Gly Arg Cys Pro Ser Gly Met Cys Cys Ser
1               5                   10                  15

Gln Phe Gly Tyr Cys Gly Lys Gly Pro Lys Tyr Cys Gly
                20                  25
```

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Val Gly Glu Cys Val Arg Gly Arg Cys Pro Ser Gly Met Cys Cys Ser
1               5                   10                  15

Gln Phe Gly Tyr Cys Gly Lys Gly Pro Lys Tyr Cys Gly Arg
                20                  25                  30
```

(2) INFORMATION FOR SEQ ID NO:7:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Ala Gly Glu Cys Val Gln Gly Arg Cys Pro Ser Gly Met Cys Cys Ser
1               5                   10                  15

Gln Phe Gly Tyr Cys Gly Arg Gly Pro Lys Tyr Cys Gly Arg Arg
                20                  25                  30
```

(2) INFORMATION FOR SEQ ID NO:8:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Glu Gln Cys Gly Ser Gln Ala Gly Gly Ala Arg Cys Ala Ser Gly Leu
1               5                   10                  15

Cys Cys Ser Lys Phe Gly Trp Cys Gly Asn Thr Asn Asp Tyr Cys Gly
                20                  25                  30

Pro Gly Asn Cys Gln Ser Gln Cys Pro Gly Gly
                35                  40
```

(2) INFORMATION FOR SEQ ID NO:9:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Glu Gln Cys Gly Arg Gln Ala Gly Gly Ala Leu Cys Pro Gly Gly Asn
1               5                   10                  15

Cys Cys Ser Gln Phe Gly Trp Cys Gly Ser Thr Thr Asp Tyr Cys Gly
            20                  25                  30

Pro Gly Cys Gln Ser Gln Cys Gly Gly
        35                  40
```

(2) INFORMATION FOR SEQ ID NO:10:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Glu Gln Cys Gly Arg Gln Ala Gly Gly Lys Leu Cys Pro Asn Asn Leu
1               5                   10                  15

Cys Cys Ser Gln Trp Gly Trp Cys Gly Ser Thr Asp Glu Tyr Cys Ser
            20                  25                  30

Pro Asp His Asn Cys Gln Ser Asn Cys Lys Asp Ser
        35                  40
```

(2) INFORMATION FOR SEQ ID NO:11:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Gln Arg Cys Gly Glu Gln Gly Ser Asn Asn Glu Cys Pro Asn Asn Leu
1               5                   10                  15

Cys Cys Ser Gln Tyr Gly Tyr Cys Gly Met Gly Gly Asp Tyr Cys Gly
            20                  25                  30

Lys Gly Cys Gln Asp Gly Ala Cys Trp Thr Ser
        35                  40
```

(2) INFORMATION FOR SEQ ID NO:12:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Gln Arg Cys Gly Ser Gln Gly Gly Gly Thr Cys Pro Ala Leu Arg
1               5                   10                  15

Cys Cys Ser Ile Trp Gly Trp Cys Gly Ala Ser Ser Pro Tyr Cys
            20                  25                  30
```

(2) INFORMATION FOR SEQ ID NO:13:

(i) SEQUENCE CHARACTERISTICS:
        (A) LENGTH: 590 base pairs
        (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:13:

CAAAAAAAAA AAATAAAGTC AAGAGTATTA ATTAGGTGAG AAAAAATGGT GAACATGAAG      60

TGTGTTGCAT TGATAGTTAT AGTTATGATG GCGTTTATGA TGGTGGATCC ATCAATGGGA     120

GTGGGAGAAT GTGTGAGAGG ACGTTGCCCA AGTGGGATGT GTTGCAGTCA GTTTGGGTAC     180

TGTGGTAAAG GCCCAAAGTA CTGTGGCCGT GCCAGTACTA CTGTGGATCA CCAAGCTGAT     240

GTTGCTGCCA CCAAAACTGC CAAGAATCCT ACCGATGCTA AACTTGCTGG TGCTGGTAGT     300

CCATGAAAGT AGTAGCTAGC TAGGTTCACG TTGGATTACC AAGCCGTGCC AGTACTACTG     360

TGGCCGTGCC AGTACTAATG TTCTCTTATA TGTCTGAAAT AAGCTCCTAT ATAAATACTA     420

GTATCTTGAT GTAATGGAGT ATTTTCATTT TGTTTTTATT TGAGTTATGA TCGTGACTTC     480

CTTGTGTTGG TTTAACTTGT ATATTGTAAT GCATCTTAAA TGCTGTCTCA AATAATTTGA     540

TGTATTAAAC ACTTGTTTTG TTTTTAATAC ATACTAAGTG CTGTAAATTC                590

(2) INFORMATION FOR SEQ ID NO:14:

(i) SEQUENCE CHARACTERISTICS:
        (A) LENGTH: 86 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Met Val Asn Met Lys Cys Val Ala Leu Ile Val Ile Val Met Met Ala
1               5                   10                  15

Phe Met Met Val Asp Pro Ser Met Gly Val Gly Glu Cys Val Arg Gly
                20                  25                  30

Arg Cys Pro Ser Gly Met Cys Cys Ser Gln Phe Gly Tyr Cys Gly Lys
            35                  40                  45

Gly Pro Lys Tyr Cys Gly Arg Ala Ser Thr Thr Val Asp His Gln Ala
        50                  55                  60

Asp Val Ala Ala Thr Lys Thr Ala Lys Asn Pro Thr Asp Ala Lys Leu
65                  70                  75                  80

Ala Gly Ala Gly Ser Pro
                85

(2) INFORMATION FOR SEQ ID NO:15:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Gln Glu Gln Cys Gly Asn Gln Ala Gly Gly Arg Ala Cys Ala Asn Arg
1               5                   10                  15

Leu Cys Cys Ser Gln Tyr Gly Tyr Cys Gly Ser Thr Arg Ala Tyr Cys
                20                  25                  30

Gly Val Gly Cys Gln Ser Asn Cys Gly Arg
            35                  40
```

(2) INFORMATION FOR SEQ ID NO:16:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 9
        (D) OTHER INFORMATION: /label= X
            /note= "Xaa = R or H"

(ix) FEATURE:
        (A) NAME/KEY: Modified-site
        (B) LOCATION: 23
        (D) OTHER INFORMATION: /label= X
            /note= "Xaa = S or N"

(xi) SEQUENCE DESCRIPTION: SEQ ID NO:16:

```
Cys Ser Ser His Asn Pro Cys Pro Xaa His Gln Cys Cys Ser Lys Tyr
1               5                   10                  15

Gly Tyr Cys Gly Leu Gly Xaa Asp Tyr Cys Gly Leu Gly Cys Arg Gly
            20                  25                  30

Gly Pro Cys Asp Arg
            35
```

(2) INFORMATION FOR SEQ ID NO:17:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
CAAGAGCAAT GCGGAAACCA AGCTGGAGGA AGAGCTTGCG CTAACAGACT TTGCTGCTCT      60

CAATACGGAT ACTGCGGATC TACTAGAGCT TACTGCGGAG TTGGATGCCA ATCTAACTGC     120

GGAAGA                                                                126
```

(2) INFORMATION FOR SEQ ID NO:18:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Cys Ser Ser His Asn Pro Cys Pro His His Gln Cys Cys Ser Lys Tyr
1               5                   10                  15

Gly Tyr Cys Gly Leu Gly Asn Asp Tyr Cys Gly Leu Gly Cys Arg Gly
            20                  25                  30

Gly Pro Cys Asp Arg
            35
```

(2) INFORMATION FOR SEQ ID NO:19:

```
    (i) SEQUENCE CHARACTERISTICS:
        (A) LENGTH: 111 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:19:

TGCTCTTCTC ACAACCCGTG CCCGAGACAC CAATGCTGCT CTAAGTACGG ATACTGCGGA      60

CTTGGATCTG ACTACTGCGG ACTTGGATGC AGAGGAGGAC CGTGCGACAG A             111

(2) INFORMATION FOR SEQ ID NO:20:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Met Ile Leu Val
1

(2) INFORMATION FOR SEQ ID NO:21:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /label= X
            /note= "Xaa = S or T"

(ix) FEATURE:
        (A) NAME/KEY: Modified-site
        (B) LOCATION: 4
        (D) OTHER INFORMATION: /label= X
            /note= "Xaa = any residue"

(ix) FEATURE:
        (A) NAME/KEY: Modified-site
        (B) LOCATION: 5
        (D) OTHER INFORMATION: /label= X
            /note= "Xaa = W, Y, or F"

(ix) FEATURE:
        (A) NAME/KEY: Modified-site
        (B) LOCATION: 7
        (D) OTHER INFORMATION: /label= X
            /note= "Xaa = W, Y, or F"

(xi) SEQUENCE DESCRIPTION: SEQ ID NO:21:

Cys Cys Xaa Xaa Xaa Gly Xaa Cys Gly
1               5

(2) INFORMATION FOR SEQ ID NO:22:

(i) SEQUENCE CHARACTERISTICS:
        (A) LENGTH: 20 amino acids
        (B) TYPE: amino acid
        (C) STRANDEDNESS: single
        (D) TOPOLOGY: linear
```

-continued

```
    (ii) MOLECULE TYPE: peptide (xi) SEQUENCE DESCRIPTION: SEQ ID NO:22:

Cys Xaa Xaa Xaa Xaa Cys Cys Xaa Xaa Xaa Xaa Xaa Cys Xaa Xaa Xaa
1               5                   10                  15

Xaa Xaa Xaa Cys
            20
```